United States Patent

Jonas et al.

[11] Patent Number: 5,747,489
[45] Date of Patent: May 5, 1998

[54] ARYLALKYL-THIADIAZINONES

[75] Inventors: Rochus Jonas; Michael Wolf, both of Darmstadt; Michael Klockow, Rossdorf, all of Germany

[73] Assignee: Merck Patent Gesellschaft mit Beschrankter Haftung, Darmstadt, Germany

[21] Appl. No.: 592,659

[22] Filed: Jan. 26, 1996

[30] Foreign Application Priority Data

Jan. 28, 1995 [DE] Germany .................. 195 02 699.3

[51] Int. Cl.$^6$ .................. A61K 31/54; C07D 285/18
[52] U.S. Cl. .................. 514/222.5; 544/8
[58] Field of Search .................. 544/8; 514/222.5

[56] References Cited

U.S. PATENT DOCUMENTS

| | | | |
|---|---|---|---|
| 4,916,128 | 4/1990 | Jonas et al. | 514/213 |
| 5,276,027 | 1/1994 | Jonas et al. | 514/222.5 |
| 5,434,149 | 7/1995 | Jonas et al. | 544/8 |

FOREIGN PATENT DOCUMENTS 351 213  7/1989  European Pat. Off.

*Primary Examiner*—John M. Ford
*Attorney, Agent, or Firm*—Millen, White, Zelano, & Branigan, P.C.

[57] ABSTRACT

Arylalkyl-thiadiazinone derivatives of the formula I

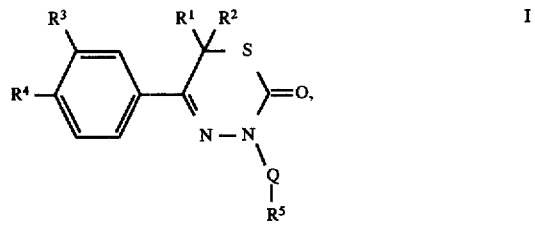

and physiologically unobjectionable salts thereof in which $R^1$, $R^2$, $R^3$, $R^4$, $R^5$ and Q have the meanings given in claim 1, exhibit phosphodiesterase IV inhibition and can be used for the therapy of asthmatic disorders.

8 Claims, No Drawings

ARYLALKYL-THIADIAZINONES

SUMMARY OF THE INVENTION

The invention relates to arylalkyl-thiadiazinone derivatives of the formula I

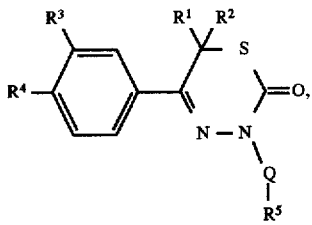

in which $R^1$ and $R^2$ each independently of one another are H or A, $R^3$ and $R^4$ each independently of one another are —OH, —OR$^{10}$, —S—R$^{10}$, —SO—R$^{10}$, —SO$_2$—R$^{10}$, Hal, —NO$_2$, —NH$_2$, —NHR$^{10}$ or —NR$^{10}$R$^{11}$, or together are methylenedioxy, $R^5$ is a phenyl radical which is unsubstituted or is mono- or disubstituted by $R^6$ and/or $R^7$, Q is absent (i.e., a single bond) or is alkylene having 1–6 carbon atoms, $R^6$ and $R^7$ each independently of one another are —NH$_2$, —NR$^8$R$^9$, —NHR$^{10}$, —NR$^{10}$R$^{11}$, —NO$_2$, Hal, —CN, —OA, —COOH or —COOA, $R^8$ and $R^9$ each independently of one another are H, acyl (e.g., alkanoyl) having 1–8 carbon atoms and which can be substituted by 1–5 fluorine and/or chlorine atoms, —COOA, —S—A, —SO—A, —SO$_2$A, —CONH$_2$, —CONHA, —CONA$_2$, —CO—COOH, —CO—COOA, —CO—CONH$_2$, —CO—CONHA or —CO—CONA$_2$, A is alkyl having 1–6 carbon atoms and which can be substituted by 1–5 fluorine and/or chlorine atoms, $R^{10}$ and $R^1$ each independently of one another are A, cycloalkyl having 3–7 carbon atoms, methylenecycloalkyl having 4–8 carbon atoms or alkenyl having 2–8 carbon atoms and Hal is F, Cl, Br or I, and physiologically unobjectionable (e.g., pharmaceutically acceptable) salts thereof.

Thiadiazinones are known, for example, from DE 37 19 031 A1 (corresponding to U.S. Pat. No. 4,916,128) and DE 41 34 893 (corresponding to U.S. Pat. No. 5,276,027).

An object of the invention was to discover novel compounds having valuable properties, especially those compounds which can be used to prepare medicaments.

It has been found that the compounds of the formula I possess valuable pharmacological properties and in addition are of good compatibility.

In particular, they exhibit phosphodiesterase IV inhibition and can be used to treat asthmatic disorders. The antiasthmatic action can be determined, for example, in accordance with the method of T. Olsson, Acta allergologica 26, 438–447 (1971).

In addition, the compounds display an inhibiting action on the formation of TNF (tumor necrosis factor) and are therefore suitable for the treatment of allergic and inflammatory diseases, autoimmune diseases and transplant-rejection reactions. They can be employed in the treatment of memory disorders. The correlation of the inhibition of the tumor necrosis factor (TNF) and the treatment of diseases which are caused by this glycoprotein is extensively described in the PCT application WO 92/19594, page 3, line 33 to page 5, line 34. In WO 93/22517, compounds are disclosed which are selective PDE IV inhibitors useful for the prophylaxis or treatment of inflammatory diseases.

The compounds can therefore be used as active medicament ingredients in human and veterinary medicine. They can additionally be employed as intermediates in the preparation of further active medicament ingredients.

The invention relates accordingly to the compounds of the formula I and to a process for their preparation, characterized in that a compound of the formula II

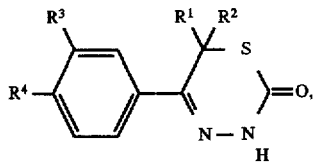

in which $R^1$, $R^2$, $R^3$ and $R^4$ have the given meanings, is reacted with a compound of the formula III

     III, in which $R^5$ and Q have the meanings given and

X is Cl, Br, OH or a reactive esterified OH group, or in that, in a compound of the formula I, one radical $R^5$ is converted into another radical $R^5$ by reducing a nitro group, acylating or alkylating a primary or a secondary amino group, or hydrolysing a cyano group, and/or in that a compound corresponding to the formula I but containing one or two free OH groups instead of $R^3$ and/or $R^4$ is, if appropriate, reacted with a compound of the formula $R^3$—X or $R^4$—X, respectively, in which $R^3$, $R^4$ and X have the meanings given, and/or a base of the formula I is converted into one of its salts by treatment with an acid.

Above and below, the radicals $R^1$, $R^2$, $R^3$, $R^4$, $R^5$, Q and X have the meanings given in the case of formulae I, II and III, unless expressly stated otherwise.

In the formulae, alkyl is preferably unbranched, has preferably 1, 2, 3 or 4 carbon atoms and is preferably methyl, and is also preferably ethyl or propyl, and is additionally preferably isopropyl, butyl, isobutyl, sec-butyl or tert-butyl, but can also be n-pentyl or isopentyl.

Cycloalkyl preferably has 3–7 carbon atoms and is preferably cyclopropyl or cyclobutyl, and additionally is preferably cyclopentyl or cyclohexyl, and furthermore is cycloheptyl.

Methylenecycloalkyl preferably has 4–8 carbon atoms and is preferably methylenecyclopropyl or methylenecyclobutyl, and is also preferably methylenecyclopentyl or methylenecyclohexyl, and additionally is methylenecycloheptyl.

Alkenyl is preferably vinyl, propenyl, isopropenyl, butenyl, isobutenyl or sec-butenyl, and is also preferably pentenyl or isopentenyl.

Alkylene is preferably unbranched and is preferably methylene or ethylene, and furthermore is preferably propylene or butylene.

Of the radicals $R^1$ and $R^2$, one is preferably hydrogen while the other is preferably propyl or butyl, but with particular preference is ethyl or methyl. Furthermore, $R^1$ and $R^2$ together are also each preferably hydrogen.

The radicals $R^3$ and $R^4$ can be identical or different and are preferably in position 3 or 4 of the phenyl ring. For example, and independently of one another, they are hydroxyl, —S—CH$_3$, —SO—CH$_3$, —SO—CH$_3$, —SO$_2$CH$_3$, F, Cl, Br or I or together are methylenedioxy. With particular preference, however, they are each methoxy, ethoxy, propoxy or else are fluoro-, difluoro- or trifluoromethoxy, or 1-fluoro-, 2-fluoro-, 1,2-difluoro-, 2,2-difluoro-, 1,2,2-trifluoro- or 2,2,2-trifluoroethoxy.

The radical R$^5$ is preferably phenyl. The phenyl radical is preferably mono- or disubstituted. Preferred substituents are cyano, nitro, amino, acetamido, trifluoroacetamido, methoxy and/or chlorine, and also preferred are methylsulfonamido, propionylamino, 2-methylpropionylamino, isobutyrylamino and/or pivalylamino, with further preferences being methoxycarbonylamino, methoxalylamino, ureido and/or carboxyl.

Q-R$^5$ is preferably benzyl, 2-, 3- or 4-nitrobenzyl, 2-, 3- or 4-cyanobenzyl, 2-, 3- or 4-aminobenzyl, 2-, 3- or 4-acetamidobenzyl, 2-, 3- or 4-trifluoroacetamidobenzyl, 2-, 3- or 4-methoxybenzyl, 2-, 3- or 4-chlorobenzyl, further preferences being 2-, 3- or 4-methylsulfonamidobenzyl, 2-, 3- or 4-propionylaminobenzyl, 2-, 3- or 4-(2-methylpropionylamino)benzyl, 2-, 3- or 4-isobutyrylaminobenzyl, 2-, 3- or 4-pivalylaminobenzyl, 2-, methoxycarbonylaminobenzyl, 2-, 3- or 4-ureidobenzyl, 2-, 3- or 4-carboxybenzyl, 2-, 3- or 4-methoxalylaminobenzyl, and also 2,3-, 2,4-, 2,5-, 2,6-, 3,4- or 3,5-dinitrobenzyl, 2,3-, 2,4-, 2,5-, 2,6-,3,4- or 3,5-diaminobenzyl, 2,3-, 2,4-, 2,5-, 2,6-, 3,4- or 3,5-diacetamidobenzyl, 2,3-, 2,4-, 2,5-, 2,6-, 3,4- or 3,5-bis(trifluoroacetamido)benzyl, 2,3-, 2,4-, 2,5-, 2,6-, 3,4- or 3,5-dimethoxybenzyl, 2,3-, 2,4-, 2,5-, 2,6-, 3,4- or 3,5-dichlorobenzyl, 2,3-, 2,4-, 2,5-, 2,6-, 3,4- or 3,5-dimethylsulfonamidobenzyl, 2,3-, 2,4-, 2,5-, 2,6-, 3,4- or 3,5-dipropionylaminobenzyl, 2,3-, 2,4-, 2,5-, 2,6-, 3,4- or 3,5-bis(2-methylpropionylamino)benzyl, 2,3-, 2,4-, 2,5-, 2,6-, 3,4- or 3,5-diisobutyrylaminobenzyl, 2,3-, 2,4-, 2,5-, 2,6-, 3,4- or 3,5-dipivalylaminobenzyl, 2,3-, 2,4-, 2,5-, 2,6-, 3,4- or 3,5-dimethoxycarbonylaminobenzyl, 2,3-, 2,4-, 2,5-, 2,6-, 3,4- or 3,5-dimethoxalylaminobenzyl, 2,3-, 2,4-, 2,5-, 2,6-, 3,4-, or 3,5- diureidobenzyl, 2,3-, 2,4-, 2,5-, 2,6-, 3,4- or 3,5-dicarboxybenzyl.

The invention relates in particular to those compounds of the formula I in which at least one of the radicals mentioned has one of the preferred meanings indicated above. Some preferred groups of compounds can be expressed by the following subformulae Ia to Ie, which correspond to the formula I and in which those radicals which are not mentioned explicitly have the meaning given in the case of the formula I, but in which

| | | |
|---|---|---|
| in Ia | R$^1$ | is H, |
| | R$^2$ | is H or A, |
| | R$^3$ | is OA; |
| in Ib | R$^1$ | is H, |
| | R$^2$ | is methyl or ethyl, |
| | R$^3$ and R$^4$ | are each OA; |
| in Ic | R$^1$ | is H |
| | R$^2$ | is methyl or ethyl, |
| | R$^3$ | is OA, |
| | R$^4$ | is mono-, di- or trifluorosubstituted alkyl having 1 to 6 carbon atoms; |
| in Id | R$^1$ | is H, |
| | R$^2$ | is methyl or ethyl, |
| | R$^3$ and R$^4$ | are OR$^{10}$ |
| | R$^5$ | is a mono- or disubstituted phenyl radical; |
| and | | |
| in Ie | R$^1$ and R$^2$ | are H, |

| | |
|---|---|
| R$^3$ and R$^4$ | are OA, and |
| R$^5$ | is a mono- or disubstituted phenyl radical. |

The compounds of the formula I are otherwise prepared by methods which are known per se and are described in the literature (for example in the standard works such as Houben-Weyl, Methoden der Organischen Chemie, [Methods of Organic Chemistry], Georg-Thieme-Verlag, Stuttgart), and under reaction conditions which are known and suitable for the reactions mentioned. In this context, use can also be made of variants which are known per se and are not mentioned in any more detail here.

In the compounds of the formula II, R$^1$, R$^2$, R$^3$ and R$^4$ have the meanings given, especially the preferred meanings given.

In the compounds of the formula III, Q is preferably methylene or ethylene, and is also preferably propylene or butylene.

In the compounds of the formula III, R$^5$ has the meanings given, especially the preferred meanings given, while X is Cl, Br, OH or a reactive esterified OH group.

If X is a reactive esterified OH group, it is preferably alkylsulfonyloxy having 1–6 carbon atoms, for example methanesulfonyloxy, or arylsulfonyloxy having 6–10 carbon atoms, for example benzene-, p-toluene- or 1- or 2-naphthalenesulfonyloxy.

If desired, the starting materials can also be formed in situ in such a way that they are not isolated from the reaction mixture but are reacted further straight away to give the compounds of the formula I. Alternatively it is possible to carry out the reaction in stages.

Some of the starting materials of the formulae II and III are known. Those which are not known can be prepared by methods which are known per se.

Thiadiazinones of the formula II and their preparation, for example, are described in German Patent Application P 41 34 893.

The compounds of the formula III are otherwise prepared by methods which are known per se and are described in the literature (for example in the standard works such as Houben-Weyl, Methoden der Organischen Chemie, [Methods of Organic Chemistry], Georg-Thieme-Verlag, Stuttgart), and under reaction conditions which are known and suitable for the reactions mentioned. In this context, use can also be made of variants which are known per se and are not mentioned in any more detail here.

In detail, the reaction of the thiadiazinones of the formula II with the compounds of the formula III takes place in the presence or absence of an inert solvent at temperatures of between about −20° and about +150°, preferably between 20° and 100°. Examples of suitable solvents are hydrocarbons such as benzene, toluene, xylenes or mesitylene; halogenated hydrocarbons such as dichloromethane, trichloroethylene or chlorobenzene; alcohols such as methanol, ethanol or isopropanol; glycols and glycol ethers such as ethylene glycol, diethylene glycol and 2-methoxyethanol; nitriles such as acetonitrile; ethers such as tetrahydrofuran (THF) or dioxane; amides such as dimethylformamide (DMF) and sulfoxides such as dimethyl sulfoxide. Mixtures of these solvents are also suitable.

Furthermore, in a compound of the formula I one radical R$^5$ can be converted into another radical R$^5$ by reducing a nitro group, acylating or alkylating a primary or a secondary amino group, or hydrolysing a cyano group.

It is also possible to react a compound which corresponds to the formula I but contains one or two free OH groups instead of $R^3$ and/or $R^4$ with a compound of the formula $R^3$—X or $R^4$—X, respectively, in which $R^3$, $R_4$ the meanings given. The OH groups are etherified by methods which are known per se and are described in standard works of the chemical literature (for example in Houben-Weyl, Methoden der Organischen Chemie, [Methods of Organic Chemistry], Georg-Thieme Verlag, Stuttgart or in Organic Reactions, John Wiley & Sons Inc., New York), under reaction conditions which are known and suitable for the reactions mentioned. In this context, use can also be made of variants which are known per se and which are not mentioned here in any more detail.

A base of the formula I which is obtained can be converted with an acid into the corresponding acid addition salt. Acids suitable for this reaction are those which give physiologically unobjectionable salts. For instance, it is possible to use inorganic acids, for example sulfuric acid, hydrohalic acids such as hydrochloric acid or hydrobromic acid, phosphoric acids such as orthophosphoric acid, nitric acid, sulfamic acid, and also organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid.

The free bases of the formula I can if desired se liberated from their salts by treatment with strong bases, such as sodium hydroxide or potassium hydroxide, sodium carbonate or potassium carbonate.

Compounds of the formula I may contain one or more centers of asymmetry. In this case they are usually in racemic form. All racemates which are obtained can be separated into their enantiomers mechanically or chemically by methods which are known per se. Preferably, diastereomers are formed from the racemic mixture by reaction with an optically active separating agent.

It is of course also possible to obtain optically active compounds of the formula I by the methods described above using starting materials which are already optically active.

This formula I embraces all stereoisomers and mixtures thereof, for example the racemates.

The invention additionally relates to the use of the compounds of the formula I and their physiologically unobjectionable salts for the production of pharmaceutical preparations, especially by a non-chemical method. In this context they can be brought, together with at least one solid, liquid and/or semiliquid excipient or auxiliary and, if desired, in combination with one or more further active ingredients, into a suitable dosage form.

The invention additionally relates to compositions, especially pharmaceutical preparations, comprising at least one compound of the formula I and/or one of its physiologically unobjectionable salts.

These preparations can be used as medicaments in human or veterinary medicine. Suitable excipients are organic or inorganic substances which are suitable for enteral (e.g., oral), parenteral or topical application and which do not react with the novel compounds, examples being water, vegetable oils, benzyl alcohols, polyethylene glycols, glycerol triacetate, gelatin, carbohydrates such as lactose or starch, magnesium stearate, talc and petroleum jelly. For oral administration use is made in particular of plain tablets, coated tablets, capsules, syrups, juices or drops, for rectal administration of suppositories, for parenteral administration of solutions, preferably oily or aqueous solutions, and also suspensions, emulsions or implants, and for topical application of ointments, creams or powders. The novel compounds can also be lyophilized and the resulting lyophilizates used, for example, to produce preparations for injection. The preparations indicated can be sterilized and/or can contain auxiliaries such as glidants, preservatives, stabilizers and/or wetting agents, emulsifiers, salts for influencing the osmotic pressure, buffer substances, colorants, flavorings and or aroma substances. If desired they can also comprise one or more other active ingredients, for example one or more vitamins.

The compounds of the formula I can be used to combat diseases, especially asthmatic disorders, and in the therapeutic treatment of the human or animal body.

In this context the substances according to the invention are generally administered in analogy to known antiasthmatics, such as Atrovent®, preferably in doses of between about 1 and 100 mg, in particular between 2 and 20 mg, per dosage unit. The daily dose is preferably between about 0.02 and 2 mg/kg of body weight. The specific dose for each particular patient depends, however, on a wide variety of factors, for example on the effectiveness of the specific compound employed, on the age, body weight, general condition of health, sex, on the diet, on the time and route of administration, on the speed of excretion, on the combination of medicaments and on the severity of the particular disease to which the therapy is applied. Adjustment of the dosage for these factors is routine and conventional in the art. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 195 02 699.3, filed Jan. 28, 1995, are hereby incorporated by reference.

In the examples, "worked up in the conventional manner" means:

water or dilute aqueous sodium hydroxide solution is added if necessary, extraction is carried out with an organic solvent such as ethyl acetate, chloroform or dichloromethane, the phases are separated, the organic phase is dried over sodium sulfate, filtered and concentrated by evaporation and the residue is purified by chromatography and/or crystallization.

EXAMPLES

Example 1

A solution of 2.8 g of 5-(3,4-dimethoxyphenyl)-6-ethyl-3,6-dihydro-1,3,4-thiadiazin-2-one ("A") [obtainable by reacting 1-(3,4-dimethoxyphenyl)-2-bromobutan-1-one with methyl hydrazinethioformate] in 150 ml of acetone is boiled with 3 g of 4-nitrobenzyl chloride in the presence of 4 g of potassium carbonate for eight hours. The insoluble residue is filtered off and the solution is concentrated. The residue is worked up in the conventional manner to give 3-(4-nitrobenzyl)-5-(3,4-dimethoxyphenyl)-6-ethyl-3,6-dihydro-1,3,4-thiadiazin-2oil.

The following compounds are obtained analogously by reacting "A":

with 3-nitrobenzyl chloride:
3-(3-nitrobenzyl)-5-(3,4-dimethoxyphenyl)-6-ethyl-3, 6-dihydro-1,3,4-thiadiazin-2-one;

with 2-nitrobenzyl chloride:
3-(2-nitrobenzyl)-5-(3,4-dimethoxyphenyl)-6-ethyl-3, 6-dihydro-1,3,4-thiadiazin-2-one;

with 2,3-dinitrobenzyl chloride:
3-(2,3-dinitrobenzyl)-5-(3,4-dimethoxyphenyl)-6-ethyl-3,6-dihydro-1,3,4-thiadiazin-2-one;

with 2,4-dinitrobenzyl chloride:
3-(2,4-dinitrobenzyl)-5-(3,4-dimethoxyphenyl)-6-ethyl-3,6-dihydro-1,3,4-thiadiazin-2-one;

with 2-methoxybenzyl chloride:
3-(2-methoxybenzyl)-5-(3,4-dimethoxyphenyl)-6-ethyl-3,6-dihydro-1,3,4-thiadiazin-2-one;

with 4-methoxybenzyl chloride:
3-(4-methoxybenzyl)-5-(3,4-dimethoxyphenyl)-6-ethyl-3,6-dihydro-1,3,4-thiadiazin-2-one, m.p. 120°;

with 2-chlorobenzyl chloride:
3-(2-chlorobenzyl)-5-(3,4-dimethoxyphenyl)-6-ethyl-3,6-dihydro-1,3,4-thiadiazin-2-one, m.p. 77°;

with 2,6-dichlorobenzyl chloride:
3-(2,6-dichlorobenzyl)-5-(3,4-dimethoxyphenyl)-6-ethyl-3,6-dihydro-1,3,4-thiadiazin-2-one, m.p. 187°;

with 4-cyanobenzyl chloride:
3-(4-cyanobenzyl)-5-(3,4-dimethoxyphenyl)-6-ethyl-3,6-dihydro-1,3,4-thiadiazin-2-one;

with 4-carboxybenzyl chloride:
3-(4-carboxybenzyl)-5-(3,4-dimethoxyphenyl)-6-ethyl-3,6-dihydro-1,3,4-thiadiazin-2-one, m.p. 106°.

Example 2

In analogy to Example 1, the reaction of 5-(3,4-dimethoxyphenyl)-3,6-dihydro-1,3,4-thiadiazin-2-one ("B") with 4-nitrobenzyl chloride gives 3-(4-nitrobenzyl)-5-(3,4-dimethoxyphenyl)-3,6-dihydro-1,3,4-thiadiazin-2-one, m.p. 155°.

The following compounds are obtained analogously by reacting "B":

with 3-nitrobenzyl chloride:
3-(3-nitrobenzyl)-5-(3,4-dimethoxyphenyl)-3,6-dihydro 1,3,4-thiadiazin-2-one;

with 2,4-dinitrobenzyl chloride:
3-(2,4-dinitrobenzyl)-5-(3,4-dimethoxyphenyl)-3,6-dihydro-1,3,4-thiadiazin-2-one;

with 4-methoxybenzyl chloride:
3-(4-methoxybenzyl)-5-(3,4-dimethoxyphenyl)-3,6-dihydro-1,3,4-thiadiazin-2-one;

with 2-chlorobenzyl chloride:
3-(2-chlorobenzyl)-5-(3,4-dimethoxyphenyl)-3,6-dihydro-1,3,4-thiadiazin-2-one;

with 2,6-dichlorobenzyl chloride:
3-(2,6-dichlorobenzyl)-5-(3,4-dimethoxyphenyl)-3,6-dihydro-1,3,4-thiadiazin-2-one;

with 4-cyanobenzyl chloride:
3-(4-cyanobenzyl)-5-(3,4-dimethoxyphenyl)-3,6-dihydro-1,3,4-thiadiazin-2-one.

Example 3

In analogy to Example 1, the reaction of 5-(3-methoxy-4-trifluoromethoxyphenyl)-6-ethyl-3,6-dihydro-1,3,4-thiadiazin-2-one with 4-nitrobenzyl chloride ("C") gives 3-(4-nitrobenzyl)-5-(3-methoxy-4-trifluoromethoxyphenyl)-6-ethyl-3,6-dihydro-1,3,4-thiadiazin-2-one.

The following compounds are obtained analogously by reacting "C":

with 5-(3-methoxy-4-difluoromethoxyphenyl)-6-ethyl-3, 6-dihydro-1,3,4-thiadiazine-2-one:
3-(4-nitrobenzyl)-5-(3-methoxy-4-difluoromethoxyphenyl)-6-ethyl-3,6-dihydro-1,3,4-thiadiazin-2-one;

with 5-(3-methoxy-4-fluoromethoxyphenyl)-6-ethyl-3,6-dihydro-1,3,4-thiadiazin-2-one:
3-(4-nitrobenzyl)-5-(3-methoxy-4-fluoromethoxyphenyl)-6-ethyl-3,6-dihydro-1,3,4-thiadiazin-2-one;

with 5-(3-difluoromethoxy-4-methoxyphenyl)-6-ethyl-3, 6-dihydro-1,3,4-thiadiazin-2-one:
3-(4-nitrobenzyl)-5-(3-difluoromethoxy-4-methoxyphenyl)-6-ethyl-3,6-dihydro-1,3,4-thiadiazin-2-one;

with 5-(3-trifluoromethoxy-4-methoxyphenyl)-6-ethyl-3,6-dihydro-1,3,4-thiadiazin-2-one:
3-(4-nitrobenzyl)-5-(3-trifluoromethoxy-4-methoxyphenyl)-6-ethyl-3,6-dihydro-1,3,4-thiadiazin-2-one;

with 5-(3-fluoromethoxy-4-methoxyphenyl)-6-ethyl-3,6-dihydro-1,3,4-thiadiazin-2-one:
3-(4-nitrobenzyl)-5-(3-fluoromethoxy-4-methoxyphenyl)-6-ethyl-3,6-dihydro-1,3,4-thiadiazin-2-one;

with 5-(3-methoxy-4-ethoxyphenyl)-6-ethyl-3,6-dihydro-1,3,4-thiadiazin-2-one:
3-(4-nitrobenzyl)-5-(3-methoxy-4-ethoxyphenyl)-6-ethyl-3,6-dihydro-1,3,4-thiadiazin-2-one;

with 5-(3-ethoxy-4-methoxyphenyl)-6-ethyl-3,6-dihydro-1,3,4-thiadiazin-2-one:
3-(4-nitrobenzyl)-5-(3-ethoxy-4-methoxyphenyl)-6-ethyl-3,6-dihydro-1,3,4-thiadiazin-2-one;

with 5-(3-hydroxy-4-methoxyphenyl)-6-ethyl-3,6-dihydro-1,3,4-thiadiazin-2-one:
3-(4-nitrobenzyl)-5-(3-hydroxy-4-methoxyphenyl)-6-ethyl-3,6-dihydro-1,3,4-thiadiazin-2-one;

with 5-(4-methylsulfonylphenyl)-6-ethyl-3,6-dihydro-1, 3,4-thiadiazin-2-one:
3-(4-nitrobenzyl)-5-(4-methylsulfonylphenyl)-6-ethyl)-3,6-dihydro-1,3,4-thiadiazin-2-one;

with 5-(3,4-methyleneoxyphenyl)-6-ethyl-3,6-dihydro-1, 3,4-thiadiazine-2-one:
3-(4-nitrobenzyl)-5-(3,4-methyleneoxyphenyl)-6-ethyl-3,6-dihydro-1,3,4-thiadiazin-2-one.

Example 4

A solution of 3.9 g of 3-(4-nitrobenzyl)-5-(3,4-dimethoxyphenyl)-6-ethyl-3,6-dihydro-1,3,4-thiadiazin-2-one in 40 ml of tetrahydrofuran is hydrogenated in the presence of Raney nickel. The catalyst is filtered off and the solution is concentrated. Recrystallization gives 3-(4-aminobenzyl)-5-(3,4-dimethoxyphenyl)-6-ethyl-3,6-dihydro-1,3,4-thiadiazin-2-one, m.p. 105°.

The following compounds are obtained analogously by reaction:

of 3-(3-nitrobenzyl)-5-(3,4-dimethoxyphenyl)-6-ethyl-3, 6-dihydro-1,3,4-thiadiazin-2-one:
3-(3-aminobenzyl)-5-(3,4-dimethoxyphenyl)-6-ethyl-3,6-dihydro-1,3,4-thiadiazin-2-one, m.p. 112°;

of 3-(2-nitrobenzyl)-5-(3,4-dimethoxyphenyl)-6-ethyl-3,6-dihydro-1,3,4-thiadiazin-2-one:
 3-(2-aminobenzyl)-5-(3,4-dimethoxyphenyl)-6-ethyl-3,6-dihydro-1,3,4-thiadiazin-2-one;

of 3-(2,3-dinitrobenzyl)-5-(3,4-dimethoxyphenyl)-6-ethyl-3,6-dihydro-1,3,4-thiadiazin-2-one:
 3-(2,3-diaminobenzyl)-5-(3,4-dimethoxyphenyl)-6-ethyl-3,6-dihydro-1,3,4-thiadiazin-2-one;

of 3-(2,4-dinitrobenzyl)-5-(3,4-dimethoxyphenyl)-6-ethyl-3,6-dihydro-1,3,4-thiadiazin-2-one:
 3-(2,4-diaminobenzyl)-5-(3,4-dimethoxyphenyl)-6-ethyl-3,6-dihydro-1,3,4-thiadiazin-2-one;

of 3-(4-nitrobenzyl)-5-(3-ethoxy-4-methoxyphenyl)-6-ethyl-3,6-dihydro-1,3,4-thiadiazin-2-one:
 3-(4-aminobenzyl)-5-(3-ethoxy-4-methoxyphenyl)-6-ethyl-3,6-dihydro-1,3,4-thiadiazin-2-one;

of 3-(4-nitrobenzyl)-5-(3-methoxy-4-difluoromethoxyphenyl)-6-ethyl-3,6-dihydro-1,3,4-thiadiazin-2-one;
 3-(4-aminobenzyl)-5-(3-methoxy-4-difluoromethoxyphenyl)-6-ethyl-3,6-dihydro-1,3,4-thiadiazin-2-one;

of 3-(4-nitrobenzyl)-5-(3-methoxy-4-fluoromethoxyphenyl)-6-ethyl-3,6-dihydro-1,3,4-thiadiazin-2-one:
 3-(4-aminobenzyl)-5-(3-methoxy-4-fluoromethoxyphenyl)-6-ethyl-3,6-dihydro-1,3,4-thiadiazin-2-one;

of 3-(4-nitrobenzyl)-5-(3-difluoromethoxy-4-methoxyphenyl)-6-ethyl-3,6-dihydro-1,3,4-thiadiazin-2-one:
 3-(4-aminobenzyl)-5-(3-difluoromethoxy-4-methoxyphenyl)-6-ethyl-3,6-dihydro-1,3,4-thiadiazin-2-one;

of 3-(4-nitrobenzyl)-5-(3-trifluoromethoxy-4-methoxyphenyl)-6-ethyl-3,6-dihydro-1,3,4-thiadiazin-2-one:
 3-(4-aminobenzyl)-5-(3-trifluoromethoxy-4-methoxyphenyl)-6-ethyl-3,6-dihydro-1,3,4-thiadiazin-2-one;

of 3-(4-nitrobenzyl)-5-(3-fluoromethoxy-4-methoxyphenyl)-6-ethyl-3,6-dihydro-1,3,4-thiadiazin-2-one:
 3-(4-aminobenzyl)-5-(3-fluoromethoxy-4-methoxyphenyl)-6-ethyl-3,6-dihydro-1,3,4-thiadiazin-2-one;

of 3-(4-nitrobenzyl)-5-(3-methoxy-4-ethoxyphenyl)-6-ethyl-3,6-dihydro-1,3,4-thiadiazin-2-one:
 3-(4-aminobenzyl)-5-(3-methoxy-4-ethoxyphenyl)-6-ethyl-3,6-dihydro-1,3,4-thiadiazin-2-one;

of 3-(4-nitrobenzyl)-5-(3-hydroxy-4-methoxyphenyl)-6-ethyl-3,6-dihydro-1,3,4-thiadiazin-2-one:
 3-(4-aminobenzyl)-5-(3-hydroxy-4-methoxyphenyl)-6-ethyl-3,6-dihydro-1,3,4-thiadiazin-2-one;

of 3-(4-nitrobenzyl)-5-(4-methylsulfonylphenyl)-6-ethyl-3,6-dihydro-1,3,4-thiadiazin-2-one:
 3-(4-aminobenzyl)-5-(4-methylsulfonylphenyl)-6-ethyl-3,6-dihydro-1,3,4-thiadiazin-2-one;

of 3-(4-nitrobenzyl)-5-(3,4-methyleneoxyphenyl)-6-ethyl-3,6-dihydro-1,3,4-thiadiazin-2-one:
 3-(4-aminobenzyl)-5-(3,4-methyleneoxyphenyl)-6-ethyl-3,6-dihydro-1,3,4-thiadiazin-2-one;

of 3-(4-nitrobenzyl)-5-(3-cyclopentyloxy-4-methoxyphenyl)-6-ethyl-3,6-dihydro-1,3,4-thiadiazin-2-one:
 3-(4-aminobenzyl)-5-(3-cyclopentyloxy-4-methoxyphenyl)-6-ethyl-3,6-dihydro-1,3,4-thiadiazin-2-one, m.p. 132°;

of 3-(4-nitrobenzyl)-5-(3,4-dimethoxyphenyl)-3,6-dihydro-1,3,4-thiadiazin-2-one:
 3-(4-aminobenzyl)-5-(3,4-dimethoxyphenyl)-3,6-dihydro-1,3,4-thiadiazin-one;

of 3-(3-nitrobenzyl)-5-(3,4-dimethoxyphenyl)-3,6-dihydro-1,3,4-thiadiazin-2-one:
 3-(3-aminobenzyl)-5-(3,4-dimethoxyphenyl)-3,6-dihydro-1,3,4-thiadiazin-2-one;

of 3-(4-nitrobenzyl)-5-(3-ethoxy-4-methoxyphenyl)-3,6-dihydro-1,3,4-thiadiazin-2-one:
 3-(4-aminobenzyl)-5-(3-ethoxy-4-methoxyphenyl)-3,6-dihydro-1,3,4-thiadiazin-2-one, m.p. 176°;

of 3-(4-nitrobenzyl)-5-(4-ethoxy-3-methoxyphenyl)-3,6-dihydro-1,3,4-thiadiazin-2-one:
 3-(4-aminobenzyl)-5-(4-ethoxy-3-methoxyphenyl)-3,6-dihydro-1,3,4-thiadiazin-2-one;

of 3-(4-nitrophenethyl)-5-(3,4-dimethoxyphenyl)-3,6-dihydro-1,3,4-thiadiazin-2-one:
 3-(4-aminophenethyl)-5-(3,4-dimethoxyphenyl)-3,6-dihydro-1,3,4-thiadiazin-2-one;

of 3-(4-nitrobenzyl)-5-(3-methoxy-4-difluoromethoxyphenyl)-3,6-dihydro-1,3,4-thiadiazin-2-one:
 3-(4-aminobenzyl)-5-(3-methoxy-4-difluoromethoxyphenyl)-3,6-dihydro-1,3,4-thiadiazin-2-one;

of 3-(4-nitrobenzyl)-5-(3-methoxy-4-fluoromethoxyphenyl)-3,6-dihydro-1,3,4-thiadiazin-2-one:
 3-(4-aminobenzyl)-5-(3-methoxy-4-fluoromethoxyphenyl)-3,6-dihydro-1,3,4-thiadiazin-2-one;

of 3-(4-nitrobenzyl)-5-(3-methoxy-4-trifluoromethoxyphenyl)-3,6-dihydro-1,3,4-thiadiazin-2-one:
 3-(4-aminobenzyl)-5-(3-methoxy-4-trifluoromethoxyphenyl)-3,6-dihydro-1,3,4-thiadiazin-2-one;

of 3-(4-nitrobenzyl)-5-(3-fluoromethoxy-4-methoxyphenyl)-3,6-dihydro-1,3,4-thiazin-2-one:
 3-(4-aminobenzyl)-5-(3-fluoromethoxy-4-methoxyphenyl)-3,6-dihydro-1,3,4-thiadiazin-2-one;

of 3-(4-nitrobenzyl)-5-(3-difluoromethoxy-4-methoxyphenyl)-3,6-dihydro-1,3,4-thiadiazin-2-one:
 3-(4-aminobenzyl)-5-(3-difluoromethoxy-4-methoxyphenyl)-3,6-dihydro-1,3,4-thiadiazin-2-one;

of 3-(4-nitrobenzyl)-5-(3-trifluoromethoxy-4-methoxyphenyl)-3,6-dihydro-1,3,4-thiadiazin-2-one:
 3-(4-aminobenzyl)-5-(3-trifluoromethoxy-4-methoxyphenyl)-3,6-dihydro-1,3,4-thiadiazin-2-one.

Example 5

10 g of 3-(4-cyanobenzyl)-5-(3,4-dihydroxyphenyl)-6-ethyl-3,6-dihydro-1,3,4-thiadiazin-2-one are added with stirring to a cooled solution of 1.3 g of NaOH in 100 ml of water and the mixture is subsequently stirred for 10 hours.

The solution is carefully heated, during which a stream of air is passed through it. Cooled sulfuric acid and water are then added. The mixture is worked up in the conventional manner to give 3-(4-carboxybenzyl)-5-(3,4- dihydroxyphenyl)-6-ethyl-3,6-dihydro-1,3,4-thiadiazin-2-one, m.p. 106°.

Example 6

0.8 ml of trifluoroacetyl chloride is added with stirring and ice cooling to a solution of 1.4 g of 3-(4-aminobenzyl)-5-(3,4-dimethoxyphenyl)-6-ethyl-3,6-dihydro-1,3,4-thiadiazin-2-one ("D") in 60 ml of dichloromethane and 1 ml of triethylamine, and the mixture is subsequently stirred for 3 hours. The solvent is removed and the residue is worked up in the conventional manner. Recrystallization from isopropanol/petroleum ether gives 1.9 g of 3-(4-trifluoroacetamidobenzyl)-5-(3,4-dimethoxyphenyl)-6-ethyl-3,6-dihydro-1,3,4-thiadiazin-2-one, m.p. 124°.

The following compounds are obtained analogously by reacting "D":

with acetyl chloride:
3-(4-acetamidobenzyl)-5-(3,4-dimethoxyphenyl)-6-ethyl-3,6-dihydro-1,3,4-thiadiazin-2-one as an oil, MS (EI) M⁺ 427;

with methylsulfonyl chloride:
3-(4-methylsulfonamidobenzyl)-5-(3,4-dimethoxyphenyl)-6-ethyl-3,6-dihydro-1,3,4-thiadiazin-2-one, amorphous, MS (EI) M⁺ 463;

with propionyl chloride:
3-(4-propionylaminobenzyl)-5-(3,4-dimethoxyphenyl)-6-ethyl-3,6-dihydro-1,3,4-thiadiazin-2-one, amorphous, MS (EI) M⁺ 441;

with isobutyryl chloride:
3-(4-isobutyrylaminobenzyl)-5-(3,4-dimethoxyphenyl)-6-ethyl-3,6-dihydro-1,3,4-thiadiazin-2-one, amorphous, MS (EI) M⁺ 455;

with methyl chloroformate:
3-(4-methoxycarbonylaminobenzyl)-5-(3,4-dimethoxyphenyl)-6-ethyl-3,6-dihydro-1,3,4-thiadiazin-2-one, m.p. 141°;

with pivalyl chloride:
3-(4-pivalylaminobenzyl)-5-(3,4-dimethoxyphenyl)-6-ethyl-3,6-dihydro-1,3,4-thiadiazin-2-one, m.p. 155°;

with cyclopentanecarbonyl chloride:
3-(4-cyclopentylcarbamoylbenzyl)-5-(3,4-dimethoxyphenyl)-6-ethyl-3,6-dihydro-1,3,4-thiadiazin-2-one, m.p. 115°;

with ethyl chloroformate:
3-(4-ethoxycarbonylaminobenzyl)-5-(3,4-dimethoxyphenyl)-6-ethyl-3,6-dihydro-1,3,4-thiadiazin-2-one, amorphous, MS (EI) M⁺ 457;

with methoxalyl chloride:
3-(4-methoxalylaminobenzyl)-5-(3,4-dimethoxyphenyl)-6-ethyl-3,6-dihydro-1,3,4-thiadiazin-2-one, amorphous, MS (EI) M⁺ 472;

with chloroformamide:
3-(4-ureidobenzyl)-5-(3,4-dimethoxyphenyl)-6-ethyl-3,6-dihydro-1,3,4-thiadiazin-2-one, m.p. 140°;

with butyryl chloride:
3-(4-butyrylaminobenzyl)-5-(3,4-dimethoxyphenyl)-6-ethyl-3,6-dihydro-1,3,4-thiadiazin-2-one, m.p. 77°;

with pentanoyl chloride:
3-(4-pentanoylaminobenzyl)-5-(3,4-dimethoxyphenyl)-6-ethyl-3,6-dihydro-1,3,4-thiadiazin-2-one;

with hexanoyl chloride:
3-(4-hexanoylaminobenzyl)-5-(3,4-dimethoxyphenyl)-6-ethyl-3,6-dihydro-1,3,4-thiadiazin-2-one, amorphous;

with pentafluoropropionyl chloride:
3-(4-pentafluoropropionylaminobenzyl)-5-(3,4-dimethoxyphenyl)-6-ethyl-3,6-dihydro-1,3,4-thiadiazin-2-one, m.p. 113°.

The following compounds are obtained analogously by reacting 3-(4-aminobenzyl)-5-(3-ethoxy-4-methoxyphenyl)-6-ethyl-3,6-dihydro-1,3,4-thiadiazin-2-one:

with trifluoroacetyl chloride:
3-(4-trifluoroacetamidobenzyl)-5-(3-ethoxy-4-methoxyphenyl)-6-ethyl-3,6-dihydro-1,3,4-thiadiazin-2-one, m.p. 155°;

with cyclopentanecarbonyl chloride:
3-(4-cyclopentylcarbamoylbenzyl)-5-(3-ethoxy-4-methoxyphenyl)-6-ethyl-3,6-dihydro-1,3,4-thiadiazin-2-one;

with acetyl chloride:
3-(4-acetamidobenzyl)-5-(3-ethoxy-4-methoxyphenyl)-6-ethyl-3,6-dihydro-1,3,4-thiadiazin-2-one;

with methylsulfonyl chloride:
3-(4-methylsulfonylamidobenzyl)-5-(3-ethoxy-4-methoxyphenyl)-6-ethyl-3,6-dihydro-1,3,4-thiadiazin-2-one;

with propionyl chloride:
3-(4-propionylaminobenzyl)-5-(3-ethoxy-4-methoxyphenyl)-6-ethyl-3,6-dihydro-1,3,4-thiadiazin-2-one, m.p. 136°;

with isobutyryl chloride:
3-(4-isobutyrylaminobenzyl)-5-(3-ethoxy-4-methoxyphenyl)-6-ethyl-3,6-dihydro-1,3,4-thiadiazin-2-one;

with methyl chloroformate:
3-(4-methoxycarbonylaminobenzyl)-5-(3-ethoxy-4-methoxyphenyl)-6-ethyl-3,6-dihydro-1,3,4-thiadiazin-2-one;

with ethyl chloroformate:
3-(4-ethoxycarbonylaminobenzyl)-5-(3-ethoxy-4-methoxyphenyl)-6-ethyl-3,6-dihydro-1,3,4-thiadiazin-2-one, m.p. 160° C.;

with methoxalyl chloride:
3-(4-methoxalylaminobenzyl)-5-(3-ethoxy-4-methoxyphenyl)-6-ethyl-3,6-dihydro-1,3,4-thiadiazin-2-one;

with chloroformamide:
3-(4-ureidobenzyl)-5-(3-ethoxy-4-methoxyphenyl)-6-ethyl-3,6-dihydro-1,3,4-thiadiazin-2-one;

with butyryl chloride:
3-(4-butyrylaminobenzyl)-5-(3-ethoxy-4-methoxyphenyl)-6-ethyl-3,6-dihydro-1,3,4-thiadiazin-2-one;

with pentanoyl chloride:
3-(4-pentanoylaminobenzyl-5-(3-ethoxy-4-methoxyphenyl)-6-ethyl-3,6-dihydro-1,3,4-thiadiazin-2-one;

with pivalyl chloride:
3-(4-pivalylaminobenzyl)-5-(3-ethoxy-4-methoxyphenyl)-6-ethyl-3,6-dihydro-1,3,4-thiadiazin-2-one;

with hexanoyl chloride:
3-(4-hexanoylaminobenzyl)-5-(3-ethoxy-4-methoxyphenyl)-6-ethyl-3,6-dihydro-1,3,4-thiadiazin-2-one;

with pentafluoropropionyl chloride:
3-(4-pentafluoropropionylaminobenzyl)-5-(3-ethoxy-4-methoxyphenyl)-6-ethyl-3,6-dihydro-1,3,4-thiadiazin-2-one.

The following compounds are obtained analogously by reacting 3-(4-aminobenzyl)-5-(3-cyclopentyloxy-4-methoxyphenyl)-6-ethyl-3,6-dihydro-1,3,4-thiadiazin-2-one:

with trifluoroacetyl chloride:
3-(4-trifluoroacetamidobenzyl)-5-(3-cyclopentyloxy-4-methoxyphenyl)-6-ethyl-3,6-dihydro-1,3,4-thiadiazin-2-one;

with acetyl chloride:
3-(4-acetamidobenzyl)-5-(3-cyclopentyloxy-4-methoxyphenyl)-6-ethyl-3,6-dihydro-1,3,4-thiadiazin-2-one, amorphous, MS (EI) M$^+$ 481;

with methylsulfonyl chloride:
3-(4-methylsulfonamidobenzyl)-5-(3-cyclopentyloxy-4-methoxyphenyl)-6-ethyl-3,6-dihydro-1,3,4-thiadiazin-2-one;

with propionyl chloride:
3-(4-propionylaminobenzyl)-5-(3-cyclopentyloxy-4-methoxyphenyl)-6-ethyl-3,6-dihydro-1,3,4-thiadiazin-2-one;

with isobutyryl chloride:
3-(4-isobutyrylaminobenzyl)-5-(3-cyclopentyloxy-4-methoxyphenyl)-6-ethyl-3,6-dihydro-1,3,4-thiadiazin-2-one;

with methyl chloroformate:
3-(4-methoxycarbonylaminobenzyl)-5-(3-cyclopentyloxy-4-methoxyphenyl)-6-ethyl-3,6-dihydro-1,3,4-thiadiazin-2-one;

with pivalyl chloride:
3-(4-pivalylaminobenzyl)-5-(3-cyclopentyloxy-4-methoxyphenyl)-6-ethyl-3,6-dihydro-1,3,4-thiadiazin-2-one;

with cyclopentanecarbonyl chloride:
3-(4-cyclopentylcarbamoylbenzyl)-5-(3-cyclopentyloxy-4-methoxyphenyl)-6-ethyl-3,6-dihydro-1,3,4-thiadiazin-2-one;

with ethyl chloroformate:
3-(4-ethoxycarbonylaminobenzyl)-5-(3-cyclopentyloxy-4-methoxyphenyl)-6-ethyl-3,6-dihydro-1,3,4-thiadiazin-2-one, m.p. 146°;

with methoxalyl chloride:
3-(4-methoxalylaminobenzyl)-5-(3-cyclopentyloxy-4-methoxyphenyl)-6-ethyl-3,6-dihydro-1,3,4-thiadiazin-2-one;

with chloroformamide:
3-(4-ureidobenzyl)-5-(3-cyclopentyloxy-4-methoxyphenyl)-6-ethyl-3,6-dihydro-1,3,4-thiadiazin-2-one;

with butyryl chloride:
3-(4-butyrylaminobenzyl)-5-(3-cyclopentyloxy-4-methoxyphenyl)-6-ethyl-3,6-dihydro-1,3,4-thiadiazin-2-one;

with pentanoyl chloride:
3-(4-pentanoylaminobenzyl)-5-(3-cyclopentyloxy-4-methoxyphenyl)-6-ethyl-3,6-dihydro-1,3,4-thiadiazin-2-one;

with hexanoyl chloride:
3-(4-hexanoylaminobenzyl)-5-(3-cyclopentyloxy-4-methoxyphenyl)-6-ethyl-3,6-dihydro-1,3,4-thiadiazin-2-one;

with pentafluoropropionyl chloride:
3-(4-pentafluoropropionylaminobenzyl)-5-(3-cyclopentyloxy-4-methoxyphenyl)-6-ethyl-3,6-dihydro-1,3,4-thiadiazin-2-one.

The following compounds are obtained analogously by reacting 3-(4-aminophenethyl)-5-(3,4-dimethoxyphenyl)-6-ethyl-3,6-dihydro-1,3,4-thiadiazin-2-one:

with trifluoroacetyl chloride:
3-(4-trifluoroacetamidophenethyl)-5-(3,4-dimethoxyphenyl)-6-ethyl-3,6-dihydro-1,3,4-thiadiazin-2-one;

with acetyl chloride:
3-(4-acetamidophenethyl)-5-(3,4-dimethoxyphenyl)-6-ethyl-3,6-dihydro-1,3,4-thiadiazin-2-one, m.p. 112°;

with methylsulfonyl chloride:
3-(4-methylsulfonamidophenethyl)-5-(3,4-dimethoxyphenyl)-6-ethyl-3,6-dihydro-1,3,4-thiadiazin-2-one;

with propionyl chloride:
3-(4-propionylaminophenethyl)-5-(3,4-dimethoxyphenyl)-6-ethyl-3,6-dihydro-1,3,4-thiadiazin-2-one;

with isobutyryl chloride:
3-(4-isobutyrylaminophenethyl)-5-(3,4-dimethoxyphenyl)-6-ethyl-3,6-dihydro-1,3,4-thiadiazin-2-one;

with methyl chloroformate:
3-(4-methoxycarbonylaminophenethyl)-5-(3,4-dimethoxyphenyl)-6-ethyl-3,6-dihydro-1,3,4-thiadiazin-2-one;

with ethyl chloroformate:
3-(4-ethoxycarbonylaminophenethyl)-5-(3,4-dimethoxyphenyl)-6-ethyl-3,6-dihydro-1,3,4-thiadiazin-2-one;

with methoxalyl chloride:
3-(4-methoxalylaminophenethyl)-5-(3,4-dimethoxyphenyl)-6-ethyl-3,6-dihydro-1,3,4-thiadiazin-2-one;

with chloroformamide:
3-(4-ureidophenethyl)-5-(3,4-dimethoxyphenyl)-6-ethyl-3,6-dihydro-1,3,4-thiadiazin-2-one;

with butyryl chloride:
3-(4-butyrylaminophenethyl)-5-(3,4-dimethoxyphenyl)-6-ethyl-3,6-dihydro-1,3,4-thiadiazin-2-one;

with cyclopentanecarbonyl chloride:
3-(4-cyclopentylcarbamoylphenethyl)-5-(3,4-dimethoxyphenyl)-6-ethyl-3,6-dihydro-1,3,4-thiadiazin-2-one;

with pentanoyl chloride:
3-(4-pentanoylaminophenethyl)-5-(3,4-dimethoxyphenyl)-6-ethyl-3,6-dihydro-1,3,4-thiadiazin-2-one;

with hexanoyl chloride:
3-(4-hexanoylaminophenethyl)-5-(3,4-dimethoxyphenyl)-6-ethyl-3,6-dihydro-1,3,4-thiadiazin-2-one;

with pentafluoropropionyl chloride:
3-(4-pentafluoropropionylaminophenethyl)-5-(3,4-dimethoxyphenyl)-6-ethyl-3,6-dihydro-1,3,4-thiadiazin-2-one;

with pivalyl chloride:
3-(4-pivalylaminophenethyl)-5-(3,4-dimethoxyphenyl)-6-ethyl-3,6-dihydro-1,3,4-thiadiazin-2-one.

The following compounds are obtained analogously by reacting 3-(3-aminobenzyl)-5-(3,4-dimethoxyphenyl)-6-ethyl-3,6-dihydro-1,3,4-thiadiazin-2-one:

with trifluoroacetyl chloride:
3-(3-trifluoroacetamidobenzyl)-5-(3,4-dimethoxyphenyl)-6-ethyl-3,6-dihydro-1,3,4-thiadiazin-2-one, amorphous, MS (EI) M$^+$ 481;

with acetyl chloride:
3-(3-acetamidobenzyl)-5-(3,4-dimethoxyphenyl)-6-ethyl-3,6-dihydro-1,3,4-thiadiazin-2-one;

with methylsulfonyl chloride:
3-(3-methylsulfonamidobenzyl)-5-(3,4-dimethoxyphenyl)-6-ethyl-3,6-dihydro-1,3,4-thiadiazin-2-one;

with propionyl chloride:
3-(3-propionylaminobenzyl)-5-(3,4-dimethoxyphenyl)-6-ethyl-3,6-dihydro-1,3,4-thiadiazin-2-one, m.p. 159°;

with cyclopentanecarboxylic acid:
3-(3-cyclopentylcarbamoylbenzyl)-5-(3,4-dimethoxyphenyl)-6-ethyl-3,6-dihydro-1,3,4-thiadiazin-2-one;

with isobutyryl chloride:
3-(3-isobutyrylaminobenzyl)-5-(3,4-dimethoxyphenyl)-6-ethyl-3,6-dihydro-1,3,4-thiadiazin-2-one;

with methyl chloroformate:
3-(3-methoxycarbonylaminobenzyl)-5-(3,4-dimethoxyphenyl)-6-ethyl-3,6-dihydro-1,3,4-thiadiazin-2-one;

with ethyl chloroformate:
3-(3-ethoxycarbonylaminobenzyl)-5-(3,4-dimethoxyphenyl)-6-ethyl-3,6-dihydro-1,3,4-thiadiazin-2-one, amorphous;

with methoxalyl chloride:
3-(3-methoxalylaminobenzyl)-5-(3,4-dimethoxyphenyl)-6-ethyl-3,6-dihydro-1,3,4-thiadiazin-2-one;

with chloroformamide:
3-(3-ureidobenzyl)-5-(3,4-dimethoxyphenyl)-6-ethyl-3,6-dihydro-1,3,4-thiadiazin-2-one;

with butyryl chloride:
3-(3-butyrylaminobenzyl)-5-(3,4-dimethoxyphenyl)-6-ethyl-3,6-dihydro-1,3,4-thiadiazin-2-one;

with pentanoyl chloride:
3-(3-pentanoylaminobenzyl)-5-(3,4-dimethoxyphenyl)-6-ethyl-3,6-dihydro-1,3,4-thiadiazin-2-one;

with hexanoyl chloride:
3-(3-hexanoylaminobenzyl)-5-(3,4-dimethoxyphenyl)-6-ethyl-3,6-dihydro-1,3,4-thiadiazin-2-one;

with pentafluoropropionyl chloride:
3-(3-pentafluoropropionylaminobenzyl)-5-(3,4-dimethoxyphenyl)-6-ethyl-3,6-dihydro-1,3,4-thiadiazin-2-one;

with pivalyl chloride:
3-(3-pivalylaminobenzyl)-5-(3,4-dimethoxyphenyl)-6-ethyl-3,6-dihydro-1,3,4-thiadiazin-2-one.

The following compounds are obtained analogously by reacting 3-(4-aminobenzyl)-5-(3-fluoromethoxy-4-methoxyphenyl)-6-ethyl-3,6-dihydro-1,3,4-thiadiazin-2-one:

with trifluoroacetyl chloride:
3-(4-trifluoroacetamidobenzyl)-5-(3-fluoromethoxy-4-methoxyphenyl)-6-ethyl-3,6-dihydro-1,3,4-thiadiazin-2-one;

with acetyl chloride:
3-(4-acetamidobenzyl)-5-(3-fluoromethoxy-4-methoxyphenyl)-6-ethyl-3,6-dihydro-1,3,4-thiadiazin-2-one;

with methylsulfonyl chloride:
3-(4-methylsulfonamidobenzyl)-5-(3-fluoromethoxy-4-methoxyphenyl)-6-ethyl-3,6-dihydro-1,3,4-thiadiazin-2-one;

with propionyl chloride:
3-(4-propionylaminobenzyl)-5-(3-fluoromethoxy-4-methoxyphenyl)-6-ethyl-3,6-dihydro-1,3,4-thiadiazin-2-one;

with isobutyryl chloride:
3-(4-isobutyrylaminobenzyl)-5-(3-fluoromethoxy-4-methoxyphenyl)-6-ethyl-3,6-dihydro-1,3,4-thiadiazin-2-one;

with methyl chloroformate:
3-(4-methoxycarbonylaminobenzyl)-5-(3-fluoromethoxy-4-methoxyphenyl)-6-ethyl-3,6-dihydro-1,3,4-thiadiazin-2-one;

with ethyl chloroformate:
3-(4-ethoxycarbonylaminobenzyl)-5-(3-fluoromethoxy-4-methoxyphenyl)-6-ethyl-3,6-dihydro-1,3,4-thiadiazin-2-one;

with methoxalyl chloride:
3-(4-methoxalylaminobenzyl)-5-(3-fluoromethoxy-4-methoxyphenyl)-6-ethyl-3,6-dihydro-1,3,4-thiadiazin-2-one;

with chloroformamide:
3-(4-ureidobenzyl)-5-(3-fluoromethoxy-4-methoxyphenyl)-6-ethyl-3,6-dihydro-1,3,4-thiadiazin-2-one;

with butyryl chloride:
3-(4-butyrylaminobenzyl)-5-(3-fluoromethoxy-4-methoxyphenyl)-6-ethyl-3,6-dihydro-1,3,4-thiadiazin-2-one;

with pentanoyl chloride:
3-(4-pentanoylaminobenzyl)-5-(3-fluoromethoxy-4-methoxyphenyl)-6-ethyl-3,6-dihydro-1,3,4-thiadiazin-2-one;

with hexanoyl chloride:
3-(4-hexanoylaminobenzyl)-5-(3-fluoromethoxy-4-methoxyphenyl)-6-ethyl-3,6-dihydro-1,3,4-thiadiazin-2-one;

with pentafluoropropionyl chloride:
3-(4-pentafluoropropionylaminobenzyl)-5-(3-fluoromethoxy-4-methoxyphenyl)-6-ethyl-3,6-dihydro-1,3,4-thiadiazin-2-one;

with pivalyl chloride:
3-(4-pivalylaminobenzyl)-5-(3-fluoromethoxy-4-methoxyphenyl)-6-ethyl-3,6-dihydro-1,3,4-thiadiazin-2-one;

with cyclopentanecarbonyl chloride:
3-(4-cyclopentylcarbamoylbenzyl)-5-(3-fluoromethoxy-4-methoxyphenyl)-6-ethyl-3,6-dihydro-1,3,4-thiadiazin-2-one.

The following compounds are obtained analogously by reacting 3-(4-aminobenzyl)-5-(3-difluoromethoxy-4-methoxyphenyl)-6-ethyl-3,6-dihydro-1,3,4-thiadiazin-2-one:

with trifluoroacetyl chloride:
3-(4-trifluoroacetamidobenzyl)-5-(3-difluoromethoxy-4-methoxyphenyl)-6-ethyl-3,6-dihydro-1,3,4-thiadiazin-2-one;

with acetyl chloride:
3-(4-acetamidobenzyl)-5-(3-difluoromethoxy-4-methoxyphenyl)6-ethyl-3,6-dihydro-1,3,4-thiadiazin-2-one;

with methylsulfonyl chloride:
3-(4-methylsulfonamidobenzyl)-5-(3-difluoromethoxy-4-methoxyphenyl)-6-ethyl-3,6-dihydro-1,3,4-thiadiazin-2-one;

with propionyl chloride:
  3-(4-propionylaminobenzyl)-5-(3-difluoromethoxy-4-methoxyphenyl)-6-ethyl-3,6-dihydro-1,3,4-thiadiazin-2-one;

with isobutyryl chloride:
  3-(4-isobutyrylaminobenzyl)-5-(3-difluoromethoxy-4-methoxyphenyl)-6-ethyl-3,6-dihydro-1,3,4-thiadiazin-2-one;

with methyl chloroformate:
  3-(4-methoxycarbonylaminobenzyl)-5-(3-difluoromethoxy-4-methoxyphenyl)-6-ethyl-3,6-dihydro-1,3,4-thiadiazin-2-one;

with ethyl chloroformate:
  3-(4-ethoxycarbonylaminobenzyl)-5-(3-difluoromethoxy-4-methoxyphenyl)-6-ethyl-3,6-dihydro-1,3,4-thiadiazin-2-one;

with methoxalyl chloride:
  3-(4-methoxalylaminobenzyl)-5-(3-difluoromethoxy-4-methoxyphenyl)-6-ethyl-3,6-dihydro-1,3,4-thiadiazin-2-one;

with chloroformamide:
  3-(4-ureidobenzyl)-5-(3-difluoromethoxy-4-methoxyphenyl)-6-ethyl-3,6-dihydro-1,3,4-thiadiazin-2-one;

with butyryl chloride:
  3-(4-butyrylaminobenzyl)-5-(3-difluoromethoxy-4-methoxyphenyl)-6-ethyl-3,6-dihydro-1,3,4-thiadiazin-2-one;

with pentanoyl chloride:
  3-(4-pentanoylaminobenzyl)-5-(3-difluoromethoxy-4-methoxyphenyl)-6-ethyl-3,6-dihydro-1,3,4-thiadiazin-2-one;

with hexanoyl chloride:
  3-(4-hexanoylaminobenzyl)-5-(3-difluoromethoxy-4-methoxyphenyl)-6-ethyl-3,6-dihydro-1,3,4-thiadiazin-2-one;

with pentafluoropropionyl chloride:
  3-(4-pentafluoropropionylaminobenzyl)-5-(3-difluoromethoxy-4-methoxyphenyl)-6-ethyl-3,6-dihydro-1,3,4-thiadiazin-2-one;

with pivalyl chloride:
  3-(4-pivalylaminobenzyl)-5-(3-difluoromethoxy-4-methoxyphenyl)-6-ethyl-3,6-dihydro-1,3,4-thiadiazin-2-one;

with cyclopentanecarbonyl chloride:
  3-(4-cyclopentylcarbamoylbenzyl)-5-(3-difluoromethoxy-4-methoxyphenyl)-6-ethyl-3,6-dihydro-1,3,4-thiadiazin-2-one.

The following compounds are obtained analogously by reacting 3-(4-aminobenzyl)-5-(3-trifluoromethoxy-4-methoxyphenyl)-6-ethyl-3,6-dihydro-1,3,4-thiadiazin-2-one:

with trifluoroacetyl chloride:
  3-(4-trifluoroacetamidobenzyl)-5-(3-trifluoromethoxy-4-methoxyphenyl)-6-ethyl-3,6-dihydro-1,3,4-thiadiazin-2-one;

with acetyl chloride:
  3-(4-acetamidobenzyl)-5-(3-trifluoromethoxy-4-methoxyphenyl)-6-ethyl-3,6-dihydro-1,3,4-thiadiazin-2-one;

with methylsulfonyl chloride:
  3-(4-methylsulfonamidobenzyl)-5-(3-trifluoromethoxy-4-methoxyphenyl)-6-ethyl-3,6-dihydro-1,3,4-thiadiazin-2-one;

with propionyl chloride:
  3-(4-propionylaminobenzyl)-5-(3-trifluoromethoxy-4-methoxyphenyl)-6-ethyl-3,6-dihydro-1,3,4-thiadiazin-2-one;

with isobutyryl chloride:
  3-(4-isobutyrylaminobenzyl)-5-(3-trifluoromethoxy-4-methoxyphenyl)-6-ethyl-3,6-dihydro-1,3,4-thiadiazin-2-one;

with methyl chloroformate:
  3-(4-methoxycarbonylaminobenzyl)-5-(3-trifluoromethoxy-4-methoxyphenyl)-6-ethyl-3,6-dihydro-1,3,4-thiadiazin-2-one;

with ethyl chloroformate:
  3-(4-ethoxycarbonylaminobenzyl)-5-(3-trifluoromethoxy-4-methoxyphenyl)-6-ethyl-3,6-dihydro-1,3,4-thiadiazin-2-one;

with methoxalyl chloride:
  3-(4-methoxalylaminobenzyl)-5-(3-trifluoromethoxy-4-methoxyphenyl)-6-ethyl-3,6-dihydro-1,3,4-thiadiazin-2-one;

with chloroformamide:
  3-(4-ureidobenzyl)-5-(3-trifluoromethoxy-4-methoxyphenyl)-6-ethyl-3,6-dihydro-1,3,4-thiadiazin-2-one;

with butyryl chloride:
  3-(4-butyrylaminobenzyl)-5-(3-trifluoromethoxy-4-methoxyphenyl)-6-ethyl-3,6-dihydro-1,3,4-thiadiazin-2-one;

with pentanoyl chloride:
  3-(4-pentanoylaminobenzyl)-5-(3-trifluoromethoxy-4-methoxyphenyl)-6-ethyl-3,6-dihydro-1,3,4-thiadiazin-2-one;

with hexanoyl chloride:
  3-(4-hexanoylaminobenzyl)-5-(3-trifluoromethoxy-4-methoxyphenyl)-6-ethyl-3,6-dihydro-1,3,4-thiadiazin-2-one;

with pentafluoropropionyl chloride:
  3-(4-pentafluoropropionylaminobenzyl)-5-(3-trifluoromethoxy-4-methoxyphenyl)-6-ethyl-3,6-dihydro-1,3,4-thiadiazin-2-one;

with pivalyl chloride:
  3-(4-pivalylaminobenzyl)-5-(3-trifluoromethoxy-4-methoxyphenyl)-6-ethyl-3,6-dihydro-1,3,4-thiadiazin-2-one;

with cyclopentanecarbonyl chloride:
  3-(4-cyclopentylcarbamoylbenzyl)-5-(3-trifluoromethoxy-4-methoxyphenyl)-6-ethyl-3,6-dihydro-1,3,4-thiadiazin-2-one.

The following compounds are obtained analogously by reacting 3-(4-aminobenzyl)-5-(3-methoxy-4-fluoromethoxyphenyl)-6-ethyl-3,6-dihydro-1,3,4-thiadiazin-2-one:

with trifluoroacetyl chloride:
  3-(4-trifluoroacetamidobenzyl)-5-(3-methoxy-4-fluoromethoxyphenyl)-6-ethyl-3,6-dihydro-1,3,4-thiadiazin-2-one;

with acetyl chloride:
  3-(4-acetamidobenzyl)-5-(3-methoxy-4-fluoromethoxyphenyl)-6-ethyl-3,6-dihydro-1,3,4-thiadiazin-2-one;

with methylsulfonyl chloride:
  3-(4-methylsulfonamidobenzyl)-5-(3-methoxy-4-fluoromethoxyphenyl)-6-ethyl-3,6-dihydro-1,3,4-thiadiazin-2-one;

with propionyl chloride:
3-(4-propionylaminobenzyl)-5-(3-methoxy-4-fluoromethoxyphenyl)-6-ethyl-3,6-dihydro-1,3,4-thiadiazin-2-one;

with isobutyryl chloride:
3-(4-isobutyrylaminobenzyl)-5-(3-methoxy-4-fluoromethoxyphenyl)-6-ethyl-3,6-dihydro-1,3,4-thiadiazin-2-one;

with methyl chloroformate:
3-(4-methoxycarbonylaminobenzyl)-5-(3-methoxy-4-fluoromethoxyphenyl)-6-ethyl-3,6-dihydro-1,3,4-thiadiazin-2-one;

with ethyl chloroformate:
3-(4-ethoxycarbonylaminobenzyl)-5-(3-methoxy-4-fluoromethoxyphenyl)-6-ethyl-3,6-dihydro-1,3,4-thiadiazin-2-one;

with methoxalyl chloride:
3-(4-methoxalylaminobenzyl)-5-(3-methoxy-4-fluoromethoxyphenyl)-6-ethyl-3,6-dihydro-1,3,4-thiadiazin-2-one;

with chloroformamide:
3-(4-ureidobenzyl)-5-(3-methoxy-4-fluoromethoxyphenyl)-6-ethyl-3,6-dihydro-1,3,4-thiadiazin-2-one;

with butyryl chloride:
3-(4-butyrylaminobenzyl)-5-(3-methoxy-4-fluoromethoxyphenyl)-6-ethyl-3,6-dihydro-1,3,4-thiadiazin-2-one;

with pentanoyl chloride:
3-(4-pentanoylaminobenzyl)-5-(3-methoxy-4-fluoromethoxyphenyl)-6-ethyl-3,6-dihydro-1,3,4-thiadiazin-2-one;

with hexanoyl chloride:
3-(4-hexanoylaminobenzyl)-5-(3-methoxy-4-fluoromethoxyphenyl)-6-ethyl-3,6-dihydro-1,3,4-thiadiazin-2-one;

with pentafluoropropionyl chloride:
3-(4-pentafluoropropionylaminobenzyl)-5-(3-methoxy-4-fluoromethoxyphenyl)-6-ethyl-3,6-dihydro-1,3,4-thiadiazin-2-one;

with pivalyl chloride:
3-(4-pivalylaminobenzyl)-5-(3-methoxy-4-fluoromethoxyphenyl)-6-ethyl-3,6-dihydro-1,3,4-thiadiazin-2-one;

with cyclopentanecarbonyl chloride:
3-(4-cyclopentylcarbamoylbenzyl)-5-(3-methoxy-4-fluoromethoxyphenyl)-6-ethyl-3,6-dihydro-1,3,4-thiadiazin-2-one.

The following compounds are obtained analogously by reacting 3-(4-aminobenzyl)-5-(3-methoxy-4-difluoromethoxyphenyl)-6-ethyl-3,6-dihydro-1,3,4-thiadiazin-2-one:

with trifluoroacetyl chloride:
3-(4-trifluoroacetamidobenzyl)-5-(3-methoxy-4-difluoromethoxyphenyl)-6-ethyl-3,6-dihydro-1,3,4-thiadiazin-2-one;

with acetyl chloride:
3-(4-acetamidobenzyl)-5-(3-methoxy-4-difluoromethoxyphenyl)-6-ethyl-3,6-dihydro-1,3,4-thiadiazin-2-one;

with methylsulfonyl chloride:
3-(4-methylsulfonamidobenzyl)-5-(3-methoxy-4-difluoromethoxyphenyl)-6-ethyl-3,6-dihydro-1,3,4-thiadiazin-2-one;

with propionyl chloride:
3-(4-propionylaminobenzyl)-5-(3-methoxy-4-difluoromethoxyphenyl)-6-ethyl-3,6-dihydro-1,3,4-thiadiazin-2-one;

with isobutyryl chloride:
3-(4-isobutyrylaminobenzyl)-5-(3-methoxy-4-difluoromethoxyphenyl)-6-ethyl-3,6-dihydro-1,3,4-thiadiazin-2-one;

with methyl chloroformate:
3-(4-methoxycarbonylaminobenzyl)-5-(3-methoxy-4-difluoromethoxyphenyl)-6-ethyl-3,6-dihydro-1,3,4-thiadiazin-2-one;

with ethyl chloroformate:
3-(4-ethoxycarbonylaminobenzyl)-5-(3-methoxy-4-difluoromethoxyphenyl)-6-ethyl-3,6-dihydro-1,3,4-thiadiazin-2-one;

with methoxalyl chloride:
3-(4-methoxalylaminobenzyl)-5-(3-methoxy-4-difluoromethoxyphenyl)-6-ethyl-3,6-dihydro-1,3,4-thiadiazin-2-one;

with chloroformamide:
3-(4-ureidobenzyl)-5-(3-methoxy-4-difluoromethoxyphenyl)-6-ethyl-3,6-dihydro-1,3,4-thiadiazin-2-one;

with butyryl chloride:
3-(4-butyrylaminobenzyl)-5-(3-methoxy-4-difluoromethoxyphenyl)-6-ethyl-3,6-dihydro-1,3,4-thiadiazin-2-one;

with pentanoyl chloride:
3-(4-pentanoylaminobenzyl)-5-(3-methoxy-4-difluoromethoxyphenyl)-6-ethyl-3,6-dihydro-1,3,4-thiadiazin-2-one;

with hexanoyl chloride:
3-(4-hexanoylaminobenzyl)-5-(3-methoxy-4-difluoromethoxyphenyl)-6-ethyl-3,6-dihydro-1,3,4-thiadiazin-2-one;

with pentafluoropropionyl chloride:
3-(4-pentafluoropropionylaminobenzyl)-5-(3-methoxy-4-difluoromethoxyphenyl)-6-ethyl-3,6-dihydro-1,3,4-thiadiazin-2-one;

with pivalyl chloride:
3-(4-pivalylaminobenzyl)-5-(3-methoxy-4-difluoromethoxyphenyl)-6-ethyl-3,6-dihydro-1,3,4-thiadiazin-2-one;

with cyclopentanecarbonyl chloride:
3-(4-cyclopentylcarbamoylbenzyl)-5-(3-methoxy-4-difluoromethoxyphenyl)-6-ethyl-3,6-dihydro-1,3,4-thiadiazin-2-one.

The following compounds are obtained analogously by reacting 3-(4-aminobenzyl)-5-(3-methoxy-4-trifluoromethoxyphenyl)-6-ethyl-3,6-dihydro-1,3,4-thiadiazin-2-one:

with trifluoroacetyl chloride:
3-(4-trifluoroacetamidobenzyl)-5-(3-methoxy-4-trifluoromethoxyphenyl)-6-ethyl-3,6-dihydro-1,3,4-thiadiazin-2-one;

with acetyl chloride:
3-(4-acetamidobenzyl)-5-(3-methoxy-4-trifluoromethoxyphenyl)-6-ethyl-3,6-dihydro-1,3,4-thiadiazin-2-one;

with methylsulfonyl chloride:
3-(4-methylsulfonamidobenzyl)-5-(3-methoxy-4-trifluoromethoxyphenyl)-6-ethyl-3,6-dihydro-1,3,4-thiadiazin-2-one;

with propionyl chloride:
  3-(4-propionylaminobenzyl)-5-(3-methoxy-4-trifluoromethoxyphenyl)-6-ethyl-3,6-dihydro-1,3,4-thiadiazin-2-one;
with isobutyryl chloride:
  3-(4-isobutyrylaminobenzyl)-5-(3-methoxy-4-trifluoromethoxyphenyl)-6-ethyl-3,6-dihydro-1,3,4-thiadiazin-2-one;
with methyl chloroformate:
  3-(4-methoxycarbonylaminobenzyl)-5-(3-methoxy-4-trifluoromethoxyphenyl)-6-ethyl-3,6-dihydro-1,3,4-thiadiazin-2-one;
with ethyl chloroformate:
  3-(4-ethoxycarbonylaminobenzyl)-5-(3-methoxy-4-trifluoromethoxyphenyl)-6-ethyl-3,6-dihydro-1,3,4-thiadiazin-2-one;
with methoxalyl chloride:
  3-(4-methoxalylaminobenzyl)-5-(3-methoxy-4-trifluoromethoxyphenyl)-6-ethyl-3,6-dihydro-1,3,4-thiadiazin-2-one;
with chloroformamide:
  3-(4-ureidobenzyl)-5-(3-methoxy-4-trifluoromethoxyphenyl)-6-ethyl-3,6-dihydro-1,3,4-thiadiazin-2-one;
with butyryl chloride:
  3-(4-butyrylaminobenzyl)-5-(3-methoxy-4-trifluoromethoxyphenyl)-6-ethyl-3,6-dihydro-1,3,4-thiadiazin-2-one;
with pentanoyl chloride:
  3-(4-pentanoylaminobenzyl)-5-(3-methoxy-4-trifluoromethoxyphenyl)-6-ethyl-3,6-dihydro-1,3,4-thiadiazin-2-one;
with hexanoyl chloride:
  3-(4-hexanoylaminobenzyl)-5-(3-methoxy-4-trifluoromethoxyphenyl)-6-ethyl-3,6-dihydro-1,3,4-thiadiazin-2-one;
with pentafluoropropionyl chloride:
  3-(4-pentafluoropropionylaminobenzyl)-5-(3-methoxy-4-trifluoromethoxyphenyl)-6-ethyl-3,6-dihydro-1,3,4-thiadiazin-2-one;
with pivalyl chloride:
  3-(4-pivalylaminobenzyl)-5-(3-methoxy-4-trifluoromethoxyphenyl)-6-ethyl-3,6-dihydro-1,3,4-thiadiazin-2-one;
with cyclopentanecarbonyl chloride:
  3-(4-cyclopentylcarbamoylbenzyl)-5-(3-methoxy-4-trifluoromethoxyphenyl)-6-ethyl-3,6-dihydro-1,3,4-thiadiazin-2-one.

The following compounds are obtained analogously by reacting 3-(4-aminobenzyl)-5-(3,4-dimethoxyphenyl)-3,6-dihydro-1,3,4-thiadiazin-2-one:

with trifluoroacetyl chloride:
  3-(4-trifluoroacetamidobenzyl)-5-(3,4-dimethoxyphenyl)-3,6-dihydro-1,3,4-thiadiazin-2-one, m.p. 176°;
with acetyl chloride:
  3-(4-acetamidobenzyl)-5-(3,4-dimethoxyphenyl)-3,6-dihydro-1,3,4-thiadiazin-2-one, m.p. 186°;
with methylsulfonyl chloride:
  3-(4-methylsulfonamidobenzyl)-5-(3,4-dimethoxyphenyl)-3,6-dihydro-1,3,4-thiadiazin-2-one;
with propionyl chloride:
  3-(4-propionylaminobenzyl)-5-(3,4-dimethoxyphenyl)-3,6-dihydro-1,3,4-thiadiazin-2-one, m.p. 186°;
with isobutyryl chloride:
  3-(4-isobutyrylaminobenzyl)-5-(3,4-dimethoxyphenyl)-3,6-dihydro-1,3,4-thiadiazin-2-one, m.p. 137°;
with methyl chloroformate:
  3-(4-methoxycarbonylaminobenzyl)-5-(3,4-dimethoxyphenyl)-3,6-dihydro-1,3,4-thiadiazin-2-one;
with ethyl chloroformate:
  3-(4-ethoxycarbonylaminobenzyl)-5-(3,4-dimethoxyphenyl)-3,6-dihydro-1,3,4-thiadiazin-2-one;
with pivalyl chloride:
  3-(4-pivalylaminobenzyl)-5-(3,4-dimethoxyphenyl)-3,6-dihydro-1,3,4-thiadiazin-2-one;
with methoxalyl chloride:
  3-(4-methoxalylaminobenzyl)-5-(3,4-dimethoxyphenyl)-3,6-dihydro-1,3,4-thiadiazin-2-one;
with chloroformamide:
  3-(4-ureidobenzyl)-5-(3,4-dimethoxyphenyl)-3,6-dihydro-1,3,4-thiadiazin-2-one;
with butyryl chloride:
  3-(4-butyrylaminobenzyl)-5-(3,4-dimethoxyphenyl)-3,6-dihydro-1,3,4-thiadiazin-2-one;
with pentanoyl chloride:
  3-(4-pentanoylaminobenzyl)-5-(3,4-dimethoxyphenyl)-3,6-dihydro-1,3,4-thiadiazin-2-one;
with hexanoyl chloride:
  3-(4-hexanoylaminobenzyl)-5-(3,4-dimethoxyphenyl)-3,6-dihydro-1,3,4-thiadiazin-2-one;
with pentafluoropropionyl chloride:
  3-(4-pentafluoropropionylaminobenzyl)-5-(3,4-dimethoxyphenyl)-3,6-dihydro-1,3,4-thiadiazin-2-one;
with cyclopentanecarbonyl chloride:
  3-(4-cyclopentylcarbamoylbenzyl)-5-(3,4-dimethoxyphenyl)-3,6-dihydro-1,3,4-thiadiazin-2-one.

The following compounds are obtained analogously by reacting 3-(4-aminobenzyl)-5-(3-ethoxy-4-methoxyphenyl)-3,6-dihydro-1,3,4-thiadiazin-2-one:

with trifluoroacetyl chloride:
  3-(4-trifluoroacetamidobenzyl)-5-(3-ethoxy-4-methoxyphenyl)-3,6-dihydro-1,3,4-thiadiazin-2-one, m.p. 188°;
with acetyl chloride:
  3-(4-acetamidobenzyl)-5-(3-ethoxy-4-methoxyphenyl)-3,6-dihydro-1,3,4-thiadiazin-2-one;
with methylsulfonyl chloride:
  3-(4-methylsulfonamidobenzyl)-5-(3-ethoxy-4-methoxyphenyl)-3,6-dihydro-1,3,4-thiadiazin-2-one;
with propionyl chloride:
  3-(4-propionylaminobenzyl)-5-(3-ethoxy-4-methoxyphenyl)-3,6-dihydro-1,3,4-thiadiazin-2-one, m.p. 184°;
with isobutyryl chloride:
  3-(4-isobutyrylaminobenzyl)-5-(3-ethoxy-4-methoxyphenyl)-3,6-dihydro-1,3,4-thiadiazin-2-one;
with methyl chloroformate:
  3-(4-methoxycarbonylaminobenzyl)-5-(3-ethoxy-4-methoxyphenyl)-3,6-dihydro-1,3,4-thiadiazin-2-one;

with ethyl chloroformate:
  3-(4-ethoxycarbonylaminobenzyl)-5-(3-ethoxy-4-methoxyphenyl)-3,6-dihydro-1,3,4-thiadiazin-2-one, m.p. 95°;
with pivalyl chloride:
  3-(4-pivalylaminobenzyl)-5-(3-ethoxy-4-methoxyphenyl)-3,6-dihydro-1,3,4-thiadiazin-2-one;
with methoxalyl chloride:
  3-(4-methoxalylaminobenzyl)-5-(3-ethoxy-4-methoxyphenyl)-3,6-dihydro-1,3,4-thiadiazin-2-one;
with chloroformamide:
  3-(4-ureidobenzyl)-5-(3-ethoxy-4-methoxyphenyl)-3,6-dihydro-1,3,4-thiadiazin-2-one;
with butyryl chloride:
  3-(4-butyrylaminobenzyl)-5-(3-ethoxy-4-methoxyphenyl)-3,6-dihydro-1,3,4-thiadiazin-2-one;
with pentanoyl chloride:
  3-(4-pentanoylaminobenzyl)-5-(3-ethoxy-4-methoxyphenyl)-3,6-dihydro-1,3,4-thiadiazin-2-one;
with hexanoyl chloride:
  3-(4-hexanoylaminobenzyl)-5-(3-ethoxy-4-methoxyphenyl)-3,6-dihydro-1,3,4-thiadiazin-2-one;
with pentafluoropropionyl chloride:
  3-(4-pentafluoropropionylaminobenzyl)-5-(3-ethoxy-4-methoxy-phenyl)-3,6-dihydro-1,3,4-thiadiazin-2-one;
with cyclopentanecarbonyl chloride:
  3-(4-cyclopentylcarbamoylbenzyl)-5-(3-ethoxy-4-methoxyphenyl)-3,6-dihydro-1,3,4-thiadiazin-2-one.

The following compounds are obtained analogously by reacting 3-(4-aminobenzyl)-5-(3-cyclopentyloxy-4-methoxyphenyl)-3,6-dihydro-1,3,4-thiadiazin-2-one:
with trifluoroacetyl chloride:
  3-(4-trifluoroacetamidobenzyl)-5-(3-cyclopentyloxy-4-methoxyphenyl)-3,6-dihydro-1,3,4-thiadiazin-2-one, m.p. 196°;
with acetyl chloride:
  3-(4-acetamidobenzyl)-5-(3-cyclopentyloxy-4-methoxyphenyl)-3,6-dihydro-1,3,4-thiadiazin-2-one;
with methylsulfonyl chloride:
  3-(4-methylsulfonamidobenzyl)-5-(3-cyclopentyloxy-4-methoxyphenyl)-3,6-dihydro-1,3,4-thiadiazin-2-one;
with propionyl chloride:
  3-(4-propionylaminobenzyl)-5-(3-cyclopentyloxy-4-methoxyphenyl)-3,6-dihydro-1,3,4-thiadiazin-2-one, m.p. 103°;
with isobutyryl chloride:
  3-(4-isobutyrylaminobenzyl)-5-(3-cyclopentyloxy-4-methoxyphenyl)-3,6-dihydro-1,3,4-thiadiazin-2-one;
with methyl chloroformate:
  3-(4-methoxycarbonylaminobenzyl)-5-(3-cyclopentyloxy-4-methoxyphenyl)-3,6-dihydro-1,3,4-thiadiazin-2-one;
with ethyl chloroformate:
  3-(4-ethoxycarbonylaminobenzyl)-5-(3-cyclopentyloxy-4-methoxyphenyl)-3,6-dihydro-1,3,4-thiadiazin-2-one, m.p. 72°;
with pivalyl chloride:
  3-(4-pivalylaminobenzyl)-5-(3-cyclopentyloxy-4-methoxyphenyl)-3,6-dihydro-1,3,4-thiadiazin-2-one;
with methoxalyl chloride:
  3-(4-methoxalylaminobenzyl)-5-(3-cyclopentyloxy-4-methoxyphenyl)-3,6-dihydro-1,3,4-thiadiazin-2-one;
with chloroformamide:
  3-(4-ureidobenzyl)-5-(3-cyclopentyloxy-4-methoxyphenyl)-3,6-dihydro-1,3,4-thiadiazin-2-one;
with butyryl chloride:
  3-(4-butyrylaminobenzyl)-5-(3-cyclopentyloxy-4-methoxyphenyl)-3,6-dihydro-1,3,4-thiadiazin-2-one;
with pentanoyl chloride:
  3-(4-pentanoylaminobenzyl)-5-(3-cyclopentyloxy-4-methoxyphenyl)-3,6-dihydro-1,3,4-thiadiazin-2-one;
with hexanoyl chloride:
  3-(4-hexanoylaminobenzyl)-5-(3-cyclopentyloxy-4-methoxyphenyl)-3,6-dihydro-1,3,4-thiadiazin-2-one;
with pentafluoropropionyl chloride:
  3-(4-pentafluoropropionylaminobenzyl)-5-(3-cyclopentyloxy-4-methoxyphenyl)-3,6-dihydro-1,3,4-thiadiazin-2-one;
with cyclopentanecarbonyl chloride:
  3-(4-cyclopentylcarbamoylbenzyl)-5-(3-cyclopentyloxy-4-methoxyphenyl)-3,6-dihydro-1,3,4-thiadiazin-2-one.

The following compounds are obtained analogously by reacting 3-(4-aminophenethyl)-5-(3,4-dimethoxyphenyl)-3,6-dihydro-1,3,4-thiadiazin-2-one:
with trifluoroacetyl chloride:
  3-(4-trifluoroacetamidophenethyl)-5-(3,4-dimethoxyphenyl)-3,6-dihydro-1,3,4-thiadiazin-2-one;
with acetyl chloride:
  3-(4-acetamidophenethyl)-5-(3,4-dimethoxyphenyl)-3,6-dihydro-1,3,4-thiadiazin-2-one;
with methylsulfonyl chloride:
  3-(4-methylsulfonamidophenethyl)-5-(3,4-dimethoxyphenyl)-3,6-dihydro-1,3,4-thiadiazin-2-one;
with propionyl chloride:
  3-(4-propionylaminophenethyl)-5-(3,4-dimethoxyphenyl)-3,6-dihydro-1,3,4-thiadiazin-2-one;
with isobutyryl chloride:
  3-(4-isobutyrylaminophenethyl)-5-(3,4-dimethoxyphenyl)-3,6-dihydro-1,3,4-thiadiazin-2-one;
with methyl chloroformate:
  3-(4-methoxycarbonylaminophenethyl)-5-(3,4-dimethoxyphenyl)-3,6-dihydro-1,3,4-thiadiazin-2-one;
with ethyl chloroformate:
  3-(4-ethoxycarbonylaminophenethyl)-5-(3,4-dimethoxyphenyl)-3,6-dihydro-1,3,4-thiadiazin-2-one;
with pivalyl chloride:
  3-(4-pivalylaminophenethyl)-5-(3,4-dimethoxyphenyl)-3,6-dihydro-1,3,4-thiadiazin-2-one;

with methoxalyl chloride:
  3-(4-methoxalylaminophenethyl)-5-(3,4-dimethoxyphenyl)-3,6-dihydro-1,3,4-thiadiazin-2-one;
with chloroformamide:
  3-(4-ureidophenethyl)-5-(3,4-dimethoxyphenyl)-3,6-dihydro-1,3,4-thiadiazin-2-one;
with butyryl chloride:
  3-(4-butyrylaminophenethyl)-5-(3,4-dimethoxyphenyl)-3,6-dihydro-1,3,4-thiadiazin-2-one;
with pentanoyl chloride:
  3-(4-pentanoylaminophenethyl)-5-(3,4-dimethoxyphenyl)-3,6-dihydro-1,3,4-thiadiazin-2-one;
with hexanoyl chloride:
  3-(4-hexanoylaminophenethyl)-5-(3,4-dimethoxyphenyl)-3,6-dihydro-1,3,4-thiadiazin-2-one;
with pentafluoropropionyl chloride:
  3-(4-pentafluoropropionylaminophenethyl)-5-(3,4-dimethoxyphenyl)-3,6-dihydro-1,3,4-thiadiazin-2-one;
with cyclopentanecarbonyl chloride:
  3-(4-cyclopentylcarbamoylphenethyl)-5-(3,4-dimethoxyphenyl)-3,6-dihydro-1,3,4-thiadiazin-2-one.

The following compounds are obtained analogously by reacting 3-(3-aminobenzyl)-5-(3,4-dimethoxyphenyl)-3,6-dihydro-1,3,4-thiadiazin-2-one:

with trifluoroacetyl chloride:
  3-(3-trifluoroacetamidobenzyl)-5-(3,4-dimethoxyphenyl)-3,6-dihydro-1,3,4-thiadiazin-2-one;
with acetyl chloride:
  3-(3-acetamidobenzyl)-5-(3,4-dimethoxyphenyl)-3,6-dihydro-1,3,4-thiadiazin-2-one;
with methylsulfonyl chloride:
  3-(4-methylsulfonamidobenzyl)-5(3,4-dimethoxyphenyl)-3,6-dihydro-1,3,4-thiadiazin-2-one;
with propionyl chloride:
  3-(3-propionylaminobenzyl)-5-(3,4-dimethoxyphenyl)-3,6-dihydro-1,3,4-thiadiazin-2-one;
with isobutyryl chloride:
  3-(3-isobutyrylaminobenzyl)-5-(3,4-dimethoxyphenyl)-3,6-dihydro-1,3,4-thiadiazin-2-one;
with methyl chloroformate:
  3-(3-methoxycarbonylaminobenzyl)-5-(3,4-dimethoxyphenyl)-3,6-dihydro-1,3,4-thiadiazin-2-one;
with ethyl chloroformate:
  3-(3-ethoxycarbonylaminobenzyl)-5-(3,4-dimethoxyphenyl)-3,6-dihydro-1,3,4-thiadiazin-2-one;
with pivalyl chloride:
  3-(3-pivalylaminobenzyl)-5-(3,4-dimethoxyphenyl)-3,6-dihydro-1,3,4-thiadiazin-2-one;
with methoxalyl chloride:
  3-(3-methoxalylaminobenzyl)-5-(3,4-dimethoxyphenyl)-3,6-dihydro-1,3,4-thiadiazin-2-one;
with chloroformamide:
  3-(3-ureidobenzyl)-5-(3,4-dimethoxyphenyl)-3,6-dihydro-1,3,4-thiadiazin-2-one;
with butyryl chloride:
  3-(3-butyrylaminobenzyl)-5-(3,4-dimethoxyphenyl)-3,6-dihydro-1,3,4-thiadiazin-2-one;
with pentanoyl chloride:
  3-(3-pentanoylaminobenzyl)-5-(3,4-dimethoxyphenyl)-3,6-dihydro-1,3,4-thiadiazin-2-one;
with hexanoyl chloride:
  3-(3-hexanoylaminobenzyl)-5-(3,4-dimethoxyphenyl)-3,6-dihydro-1,3,4-thiadiazin-2-one;
with pentafluoropropionyl chloride:
  3-(3-pentafluoropropionylaminobenzyl)-5-(3,4-dimethoxyphenyl)-3,6-dihydro-1,3,4-thiadiazin-2-one;
with cyclopentanecarbonyl chloride:
  3-(3-cyclopentylcarbamoylbenzyl)-5-(3,4-dimethoxyphenyl)-3,6-dihydro-1,3,4-thiadiazin-2-one.

Example 7

1.5 ml of butyl bromide dissolved in 20 ml of dichloromethane is added with stirring and cooling to a solution of 1.4 g of 3-(4-aminobenzyl)-5-(3,4-dimethoxyphenyl)-6-ethyl-3,6-dihydro-1,3,4-thiadiazin-2-one in 60 ml of dichloromethane and 1 ml of triethylamine, and the mixture is subsequently stirred for 3 hours. The solvent is removed and the residue is worked up in the conventional manner, to give 3-(4-N,N-dibutylaminobenzyl)-5-(3,4-dimethoxyphenyl)-6-ethyl-3,6-dihydro-1,3,4-thiadiazin-2-one.

Example 8

One equivalent of trifluoromethyl iodide is added to a solution of 1.4 g of 3-(4-propionylaminobenzyl)-5-(3-hydroxy- 4-methoxyphenyl)-6- ethyl-3 ,6-dihydro-1,3,4-thiadiazin-2-one [obtainable by reacting 3-(4-aminobenzyl)-5-(3-hydroxy-4-methoxyphenyl)-6-ethyl-3,6-dihydro-1,3,4-thiadiazin-2-one with propionyl chloride] in THF, and the mixture is then boiled for two hours.

The solvent is subsequently removed and the residue is worked up in the conventional manner, to give 3-(4-propionylamino)-5-(3-trifluoromethoxy-4-methoxyphenyl)-6-ethyl-3,6-dihydro-1,3,4-thiadiazin-2-one.

Example 9

The following compounds are obtained analogously by reaction of 3-(2-nitrobenzyl)-5-(3,4-dimethoxy)-3,6-dihydro-1,3,4-thiadiazin-2-one:
  3-(2-aminobenzyl)-5-(3,4-dimethoxy)-3,6-dihydro-1,3,4-thiadiazin-2-one ("E"), m.p. 127°;

of 3-(4-nitrobenzyl)-5-(3-propoxy-4-methoxy)-3,6-dihydro-1,3,4-thiadiazin-2-one:
  3-(4-aminobenzyl)-5-(3-propoxy-4-methoxy)-3,6-dihydro-1,3,4-thiadiazin-2-one, m.p. 125°;

of 3-(4-nitrobenzyl)-5-(3-cyclopentyloxy-4-methoxy)-3,6-dihydro-1,3,4-thiadiazin-2-one:
  3-(4-aminobenzyl)-5-(3-cyclopentyloxy-4-methoxy)-3,6-dihydro-1,3,4-thiadiazin-2-one, m.p. 123°.

Example 10

The following compounds are obtained in analogy to Example 6 by reacting "E":

with acetyl chloride:
  3-(2-acetamidobenzyl)-5-(3,4-dimethoxy)-3,6-dihydro-1,3,4-thiadiazin-2-one, m.p. 210°;

with trifluoroacetyl chloride:

3-(2-trifluoroacetamidobenzyl)-5-(3,4-dimethoxy)-3,6-dihydro-1,3,4-thiadiazin-2-one, m.p. 200°.

The following compounds are obtained by reacting 3-(4-aminobenzyl)-5-(3-propoxy-4-methoxy)-3,6-dihydro-1,3,4-thiadiazin-2-one:

with acetyl chloride:

3-(4-acetamidobenzyl)-5-(3-propoxy-4-methoxy)-3,6-dihydro-1,3,4-thiadiazin-2-one, no defined melting point, amorphous;

with propionyl chloride:

3-(4-propionylaminobenzyl)-5-(3-propoxy-4-methoxy)-3,6-dihydro-1,3,4-thiadiazin-2-one, m.p. 150°;

with trifluoroacetyl chloride:

3-(4-trifluoroacetamido)-5-(3-propoxy-4-methoxy)-3,6-dihydro-1,3,4-thiadiazin-2-one, m.p. 167°.

The examples which follow relate to pharmaceutical preparations:

Example A
Injection vials

A solution of 100 g of an active ingredient of the formula I and 5 g of disodium-hydrogen phosphate in 3 l of double-distilled water is adjusted to a pH of 6.5 using 2 N hydrochloric acid, subjected to sterile filtration, dispensed into injection vials and lyophilized under sterile conditions and the vials are sealed in a sterile manner. Each injection vial contains 5 mg of active ingredient.

Example B
Suppositories

A mixture of 20 g of an active ingredient of the formula I is melted with 100 g of soya lecithin and 1400 g of cocoa butter and the mixture is poured into molds and allowed to cool. Each suppository contains 20 mg of active ingredient.

Example C
Solution

A solution is prepared from 1 g of an active ingredient of the formula I, 9.38 g of $NaH_2PO_4 \cdot 2\ H_2O$, 28.48 g of $Na_2HPO_4 \cdot 12\ H_2O$ and 0.1 g of benzalkonium chloride in 940 ml of double-distilled water. The solution is adjusted to a pH of 6.8, made up to 1 l and sterilized by irradiation. This solution can be used in the form of eyedrops.

Example D
Ointment 500 mg of an active ingredient of the formula I are mixed with 99.5 g of petroleum jelly under aseptic conditions.

Example E
Tablets

A mixture of 1 kg of active ingredient of the formula I, 4 kg of lactose, 1.2 kg of potato starch, 0.2 kg of talc and 0.1 kg of magnesium stearate is pressed in a customary manner to give tablets, such that each tablet contains 10 mg of active ingredient.

Example F
Coated tablets

Tablets are pressed in analogy to Example E and are when coated in a customary manner with a coating of sucrose, potato starch, talc, gum tragacanth and colorant.

Example G
Capsules

Hard gelatin capsules are filled in a customary manner with 2 kg of active compound of the formula I such that each capsule contains 20 mg of the active ingredient.

Example H
Ampoules

A solution of 1 kg of active ingredient of the formula I in 60 l of double-distilled water is subjected to sterile filtration, dispensed into ampoules and lyophilized under sterile conditions, and the ampoules are sealed in a sterile manner. Each ampoule contains 10 mg of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An arylalkyl-thiadiazinone compound of formula I

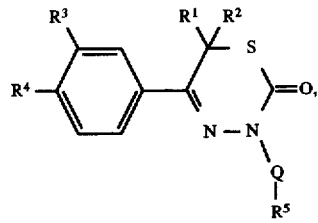

wherein $R^1$ and $R^2$ are each independently H or A, $R^3$ and $R^4$ are each independently —OH, —$OR^{10}$, —S—$R^{10}$, —SO—$R^{10}$, —$SO_2$—$R^{10}$, Hal, methylenedioxy, —$NO_2$, —$NH_2$, —$NHR^{10}$ or —$NR^{10}R^{11}$, $R^5$ is a phenyl radical which is unsubstituted or is mono- or disubstituted by $R^6$ and/or $R^7$, Q is absent or is $C_{1-6}$-alkylene, $R^6$ and $R^7$ are each independently —$NH_2$, —$NR^8R^9$, —$NHR_{10}$, —$NR^{10}R^{11}$, —$NO_2$, Hal, —CN, —OA, —COOH or —COOA, $R^8$ and $R^9$ are each independently H, $C_{1-8}$-alkanoyl optionally substituted by 1–5 fluorine and/or chlorine atoms, —COOA, —S—A, —SO—A, —$SO_2A$, —$CONH_2$, —CONHA, —$CONA_2$, —CO—COOH, —CO—COOA, —CO—$CONH_2$, —CO—CONHA or —CO—$CONA_2$, A is $C_{1-6}$-alkyl optionally substituted by 1–5 fluorine and/or chlorine atoms, $R^{10}$ and $R^{11}$ are each independently A, $C_{3-7}$—cycloalkyl, $C_{4-8}$-methylenecycloalkyl or $C_{2-8}$-alkenyl, and Hal is F, Cl, Br or I, or a physiologically acceptable salt thereof.

2. A compound according to claim 1, wherein $R^1$ is H, $R^2$ is H or A, and $R^3$ is OA.

3. A compound according to claim 1, wherein $R^1$ is H, $R^2$ is methyl or ethyl, and $R^3$ and $R^4$ are each OA.

4. A compound according to claim 1, wherein $R^1$ is H, $R^2$ is methyl or ethyl, $R^3$ is OA, and $R^4$ is mono-, di- or trifluorosubstituted alkyl having 1 to 6 carbon atoms.

5. A compound according to claim 1, wherein $R^1$ is H, $R^2$ is methyl or ethyl, $R^3$ and $R^4$ are $OR^{10}$, and $R^5$ is a mono-or disubstituted phenyl radical.

6. A compound according to claim 1, wherein $R^1$ and $R^2$ are H, $R^3$ and $R^4$ are OA, and $R^5$ is a mono- or disubstituted phenyl radical.

7. A compound according to claim 1, which is:

(a) 3-(4-Nitrobenzyl)-5-(3,4-dimethoxyphenyl)-6-ethyl-3,6-dihydro-1,3,4-thiadiazin-2-one;

(b) 3-(4-aminobenzyl)-5-(3,4-dimethoxyphenyl)-6-ethyl-3,6-dihydro-1,3,4-thiadiazin-2-one;

(c) 3-(4-trifluoroacetamidobenzyl)-5-(3,4-dimethoxyphenyl)-6-ethyl-3,6-dihydro-1,3,4-thiadiazin-2-one;

(d) 3-(4-acetamidobenzyl)-5-(3,4-dimethoxy-phenyl)-3,6-dihydro-1,3,4-thiadiazin-2-one;

(e) 3-(4-methoxybenzyl)-5-(3,4-dimethoxyphenyl)-6-ethyl-3,6-dihydro-1,3,4-thiadiazin-2-one; or (f) 3-(2,6-dichlorobenzyl)-5-(3,4-dimethoxyphenyl)-6-ethyl-3,6-dihydro-1,3,4-thiadiazin-2-one.

8. A pharmaceutical composition comprising one or more compounds of formula I according to claim 1 or physiologically acceptable salts thereof, and a pharmaceutically acceptable carrier.

* * * * *